(12) United States Patent
Vo et al.

(10) Patent No.: US 7,414,030 B2
(45) Date of Patent: *Aug. 19, 2008

(54) 6-11 BICYCLIC ERYTHROMYCIN DERIVATIVES

(75) Inventors: Nha Huu Vo, Southborough, MA (US); Guoqiang Wang, Belmont, MA (US); Guoyou Xu, Newton, MA (US); Ying Hou, Everett, MA (US); Ying Sun, Waltham, MA (US); Ly Tam Phan, Quing, MA (US); Zhe Wang, Hockessin (DE); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 262 days.

This patent is subject to a terminal disclaimer.

(21) Appl. No.: 11/029,640

(22) Filed: Jan. 5, 2005

(65) Prior Publication Data
US 2005/0187169 A1 Aug. 25, 2005

Related U.S. Application Data

(60) Provisional application No. 60/534,885, filed on Jan. 7, 2004.

(51) Int. Cl.
*A61K 31/70* (2006.01)
*C07H 17/08* (2006.01)
(52) U.S. Cl. .......................... 514/29; 536/7.2; 536/7.3; 536/7.4
(58) Field of Classification Search .................. 536/7.2, 536/7.3, 7.4; 514/29
See application file for complete search history.

(56) References Cited

U.S. PATENT DOCUMENTS 4,921,839 A 5/1990 Brain et al.

(Continued)

FOREIGN PATENT DOCUMENTS

EP 596802 5/1994

(Continued)

OTHER PUBLICATIONS

U.S. Appl. No. 11/257,680, filed Oct. 25, 2005, Wang et al.

(Continued)

*Primary Examiner*—Elli Peselev
(74) *Attorney, Agent, or Firm*—Carolyn S. Elmore; Elmore Patent Law Group

(57) ABSTRACT

The present invention discloses compounds of formulaes I, II, III, or IV, or a racemate, enantiomer, regioisomer, salt, ester or prodrug thereof:

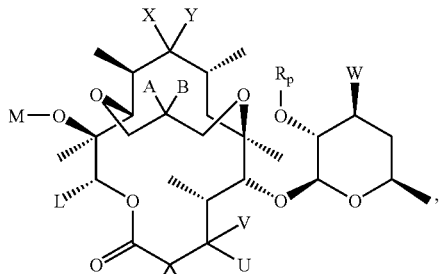

(I)

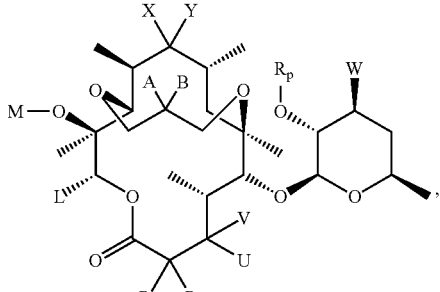

(II)

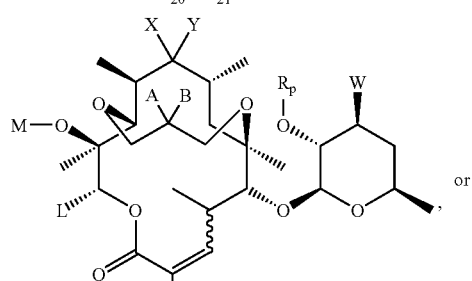

(III)

or

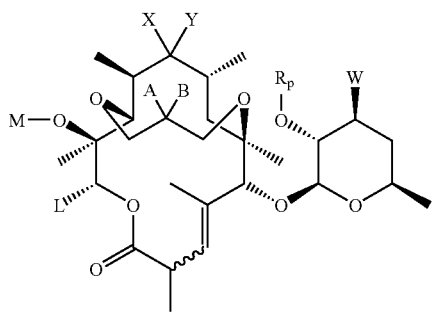

(IV)

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

25 Claims, No Drawings

U.S. PATENT DOCUMENTS

| | | | |
|---|---|---|---|
| 4,990,602 A | 2/1991 | Morimoto et al. | |
| 5,202,434 A | 4/1993 | Wilkening | |
| 5,403,923 A | 4/1995 | Kashimura et al. | |
| 5,441,939 A | 8/1995 | Yang | |
| 5,444,051 A | 8/1995 | Agouridas et al. | |
| 5,527,780 A | 6/1996 | Agouridas et al. | |
| 5,556,839 A | 9/1996 | Greene et al. | |
| 5,631,355 A | 5/1997 | Asaka et al. | |
| 5,780,605 A | 7/1998 | Or et al. | |
| 5,866,549 A | 2/1999 | Or et al. | |
| 5,922,683 A | 7/1999 | Or et al. | |
| 5,969,161 A | 10/1999 | Bonnet et al. | |
| 6,046,171 A | 4/2000 | Or et al. | |
| 6,054,435 A | 4/2000 | Or et al. | |
| 6,075,011 A | 6/2000 | Or et al. | |
| 6,075,133 A | 6/2000 | Or et al. | |
| 6,124,269 A | 9/2000 | Phan et al. | |
| 6,274,715 B1 | 8/2001 | Or et al. | |
| 6,355,620 B1 | 3/2002 | Ma et al. | |
| 6,399,582 B1 | 6/2002 | Hlasta et al. | |
| 6,645,941 B1 | 11/2003 | Wang et al. | |
| 6,764,998 B1 | 7/2004 | Wang et al. | |
| 6,777,543 B2 * | 8/2004 | Wu et al. | 536/7.4 |
| 6,878,691 B2 | 4/2005 | Or et al. | |
| 7,273,853 B2 * | 9/2007 | Or et al. | 514/29 |
| 2004/0053861 A1 | 3/2004 | Or et al. | |
| 2004/0157787 A1 | 8/2004 | Or et al. | |
| 2004/0171818 A1 | 9/2004 | Xu et al. | |
| 2004/0266998 A1 | 12/2004 | Or et al. | |
| 2005/0009761 A1 | 1/2005 | Or et al. | |
| 2005/0009763 A1 | 1/2005 | Or et al. | |
| 2005/0014707 A1 | 1/2005 | Wang et al. | |
| 2005/0159370 A1 | 7/2005 | Or et al. | |
| 2005/0171033 A1 | 8/2005 | Qiu et al. | |

FOREIGN PATENT DOCUMENTS

| | | |
|---|---|---|
| WO | WO 97/10251 | 3/1997 |
| WO | WO 97/42205 | 11/1997 |
| WO | WO 99/21864 | 5/1999 |
| WO | WO 00/62783 | 10/2000 |
| WO | WO 00/78773 | 12/2000 |
| WO | WO 01/40241 | 6/2001 |
| WO | WO 03/095466 A1 | 11/2003 |
| WO | WO 03/097659 A1 | 11/2003 |

OTHER PUBLICATIONS

U.S. Appl. No. 11/154,260, filed Jun. 16, 2005, Deqiang Niu, et al.
U.S. Appl. No. 11/057,476, filed Feb. 14, 2005, Datong Tang, et al.
U.S. Appl. No. 11/122,215, filed May 4, 2005, Guoqiang Wang, et al.
8$^{th}$ International Antibacterial Drug Discovery and Development Summit, *Strategic Research Institute,* Mar. 24-25, 2003, Princeton, NJ.

* cited by examiner

6-11 BICYCLIC ERYTHROMYCIN DERIVATIVES

RELATED APPLICATION

This application claims the benefit of U.S. Provisional Application No. 60/534,885, filed on Jan. 7, 2004. The entire teachings of the above application are incorporated herein by reference.

TECHNICAL FIELD

The present invention relates to novel semisynthetic macrolides having antibacterial activity and useful in the treatment and prevention of bacterial infections. More particularly, the invention relates to 6-11 bicyclic macrolide, ketolide, and anhydrolide derivatives, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin, clarithromycin, and azithromycin. Macrolides possessing a 3-oxo moiety in place of the 3-cladinose sugar are known as ketolides and have shown enhanced activity towards gram-negative bacteria and macrolide resistant gram-positive bacteria. Macrolides possessing a degree of unsaturation between carbons 2 and 3 or between carbons 3 and 4 of the erythromycin macrocycle are known as anhydrolides. The search for macrolide compounds which are active against $MLS_B$-resistant strains ($MLS_B$=Macrolides-Lincosamides-type B Streptogramines) has become a major goal, together with retaining the overall profile of the macrolides in terms of stability, tolerance and pharmacokinetics.

International Application WO 97/42205 of Elliott et al, published Nov. 13, 1997, discloses 3-descladinose-2,3-anhydroerythromycin derivatives having a cyclic carbamate and cyclic carbazate basic nuclear structure. Further details were also disclosed in *J. Med Chem.*, 41, pp 1651-1659(1998) and *J. Med Chem.*, 41, pp 1660-1670 (1998) by Elliott et al, and by Griesgraber et al, respectively.

U.S. Pat. No. 5,444,051 discloses certain 6-O-substituted-3-oxoerythromycin A derivatives. PCT application WO 97/10251, published Mar. 20, 1997, discloses intermediates useful for preparation of 6-O-methyl 3-descladinose erythromycin derivatives. U.S. Pat. No. 5,631,355 discloses certain tricyclic 6-O-methyl 3-oxo erythromycin derivatives. U.S. Pat. No. 5,527,780 discloses certain bicyclic 6-O-methyl-3-oxo erythromycin A derivatives (Agouridas, ROUSSEL) corresponding to EP application 596802, published May 11, 1994. U.S. Pat. Nos. 5,866,549 and 6,075,011, and PCT application WO 00/78773, published Dec. 28, 2000, disclose certain 6-O-substituted erythromycin derivatives. U.S. Pat. No. 6,124,269 and PCT application WO 00/62783, published Oct. 26, 2000, disclose certain 2-halo-6-O-substituted ketolide derivatives. U.S. Pat. No. 6,046,171 and PCT application WO 99/21864, published May 6, 1999, disclose certain 6,11-bridged erythromycin derivatives.

PCT Application WO 03/095466 A1, published Nov. 20, 2003 and PCT Application WO 03/097659 A1, published Nov. 27, 2003 disclose a series of bicyclic erythromycin derivatives.

SUMMARY OF THE INVENTION

The present invention provides a novel class of C6-C11 bridged erythromycin derivatives which possess antibacterial activity.

In one aspect of the present invention there are provided novel bridged erythromycin compounds represented by the formulae as illustrated below:

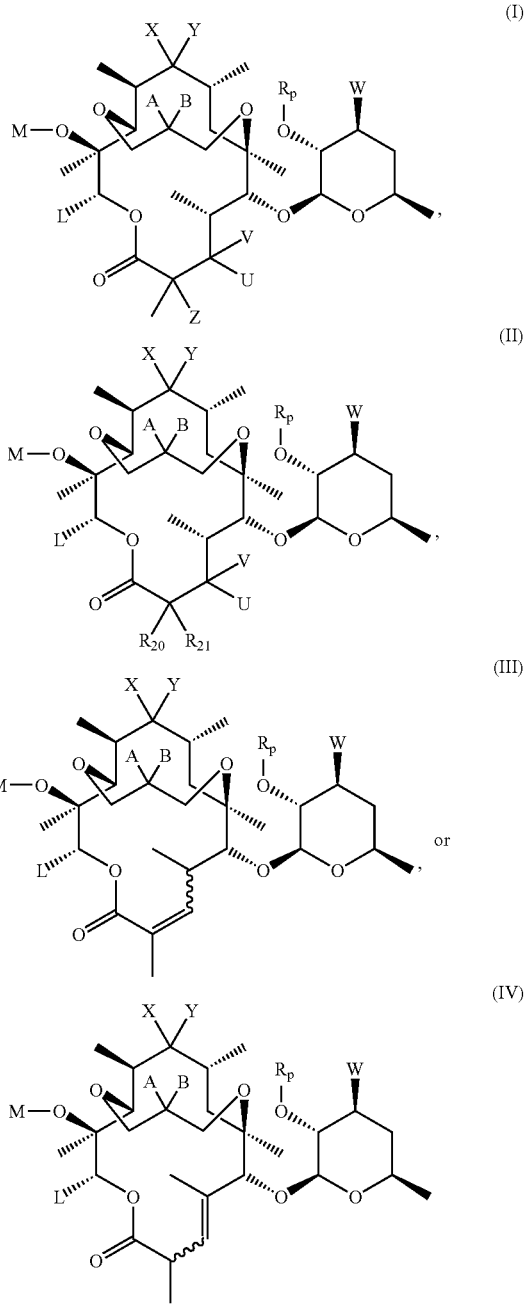

or their racemates, enantiomers, regioisomers, salts, esters or prodrugs thereof, wherein A and B are independently selected from the group consisting of: hydrogen, deuterium, halogen, $R_1$, $OR_1$, $S(O)_nR_1$, $-NR_1C(O)R_1$, $-NR_1C(O)NR_3R_4$, $-NHS(O)_nR_1$, $-CONR_3R_4$, and $NR_3R_4$;

$R_1$ and $R_2$ are independently selected from the group consisting of: hydrogen, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

Each of $R_3$ and $R_4$ is independently selected from the group consisting of: hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, a substituted, or unsubstituted heterocyclic group; or can be taken together with the nitrogen atom to which they are attached to form a substituted or unsubstituted heterocyclic or heteroaromatic ring;

Each of $R_{20}$ and $R_{21}$ is independently selected from the group consisting of: hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, a substituted, or unsubstituted heterocyclic group, provided that $R_{20}$ and $R_{21}$ cannot be methyl and hydrogen, methyl and methyl, or methyl and halogen;

or $R_{20}$ and $R_{21}$ taken together with the carbon atom to which they are attached form a substituted or unsubstituted alicylic or substituted or unsubstituted heterocyclic ring;

or A and B, taken together with the carbon atom to which they are attached, form a substituted or unsubstituted alicyclic, aromatic, heterocyclic or heteroaromatic ring;

or A and B, taken together with the carbon atom to which they are attached, are selected from the group consisting of: CO, C=$CHR_1$, C=$NR_1$, C=$NOR_1$, C=$NO(CH_2)_mR_1$, C=$NNHR_1$, C=$NNHCOR_1$, C=$NNHCONR_1R_2$, C=$NNHS(O)_nR_1$, or C=N—N=$CHR_1$;

M is selected from the group consisting of: hydrogen, $R_1$, $C(O)R_1$, $S(O)_nR_1$, or $C(O)NR_3R_4$; provided that M is not hydrogen for compounds of formula I;

L is selected from the group consisting of: hydrogen, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

X and Y are independently selected from the group consisting of: hydrogen, deuterium, halogen, $R_1$, $OR_1$, $S(O)_nR_1$, $-NR_1C(O)R_1$, $-NR_1C(O)NR_3R_4$, $-NR_1S(O)_nR_1$, $-C(O)NR_3R_4$, and $-NR_3R_4$;

or X and Y, taken together with the carbon atom to which they are attached, are selected from the group consisting of: CO, C=$CHR_1$, C=$NR_1$, C=$NC(O)R_1$, C=$NOR_1$, C=$NO(CH_2)_mR_1$, C=$NNHR_1$, C=$NNHCOR_1$, C=$NNHCONR_1R_2$, C=$NNHS(O)_nR_1$, C=N—N=$CHR_1$, C=N—$NO_2$, or C=N—ONO;

one of U or V is hydrogen and the other is independently selected from the group consisting of: $R_1$, $OR_1$, $OC(O)R_1$, $OC(O)NR_3R_4$, $S(O)_nR_1$, or

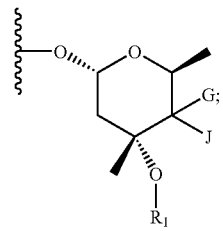

or U and V, taken together with the carbon atom to which they are attached, are C=O;

one of J or G is hydrogen and the other is selected from: $R_1$, $OR_1$, or $NR_3R_4$;

or, J and G, taken together with the carbon atom to which they are attached, are selected from: C=O, C=$NR_1$, C=$NOR_1$, C=$NO(CH_2)_mR_1$, C=$NNHR_1$, C=$NNHCOR_1$, C=$NNHCONR_1R_2$, C=$NNHS(O)_nR_1$, or C=N—N=$CHR_1$;

W is $NR_3R_4$;

Z is hydrogen, alkyl or halogen;

$R_p$ is hydrogen, hydroxy protecting group or hydroxy prodrug group;

m is an integer; and n is 0, 1, or 2.

In another embodiment of the present invention there are disclosed pharmaceutical compositions comprising a therapeutically effective amount of any compound of the present invention in combination with a pharmaceutically acceptable carrier or excipient. In yet another embodiment of the invention are methods of treating antibacterial infections in a subject with said pharmaceutical compositions. Suitable carriers and methods of formulation are also disclosed.

In a further aspect of the present invention there are provided processes for the preparation of any 6,11 bridged erythromycin derivative of formulas I, II, III, or IV via any synthetic route delineated herein.

DETAILED DESCRIPTION OF THE INVENTION

A first embodiment of the present invention is a compound of formula I as defined herein, or a racemate, enantiomer, regioisomer, pharmaceutically acceptable salt, ester, or prodrug thereof.

A second embodiment of the present invention is a compound of formula II as defined herein, or a racemate, enantiomer, regioisomer, pharmaceutically acceptable salt, ester, or prodrug thereof.

A third embodiment of the present invention is a compound of formula III as defined herein, or a racemate, enantiomer, regioisomer, pharmaceutically acceptable salt, ester, or prodrug thereof.

A fourth embodiment of the present invention is a compound of formula IV as defined herein, or a racemate, enantiomer, regioisomer, pharmaceutically acceptable salt, ester, or prodrug thereof.

Representative subgenera of the present invention are:

A compound according to formula I, wherein M is not hydrogen;

A compound according to formula I, II, III, or IV wherein A and B taken together with the carbon atom to which they are attached are C=N—O—$CH_2$—$R_1$, where $R_1$ is:

1. a substituted pyridyl;
2. a pyridyl substituted with pyrazole;
3. C≡C-(pyridyl) or C≡C-(substituted pyridyl);

4. C≡C-(2-amino-6-pyridyl);
5. a pyridyl substituted with a substituted pyridyl;
6. a substituted thiophenyl; or
7. a thiophenyl substituted with a substituted pyridyl;

A compound according to formula I, II, III, or IV, wherein A and B taken together with the carbon atom to which they are attached are C=CH—$R_1$;

A compound according to formula I, II, III, or IV, wherein A and B taken together with the carbon atom to which they are attached are C=CH—$R_1$ and X and Y taken together with the carbon atom to which they are attached are C=N-Q, where Q is $R_1$, C(O)$R_1$, O$R_1$, O(CH$_2$)$_m$$R_1$, NH$R_1$, NHCO$R_1$, NHCONR$_1$R$_2$, NHS(O)$_n$R$_1$, N=CH$R_1$, NO$_2$, or ONO;

A compound according to formula I, II, III, or IV wherein A and B taken together with the carbon atom to which they are attached are C=CH—$R_1$ and X and Y taken together with the carbon atom to which they are attached are C=N—Ac;

A compound according to formula I, II, III, or IV wherein X and Y taken together with the carbon atom to which they are attached are C=N—$R_1$;

A compound according to formula I, II, III, or IV wherein X and Y taken together with the carbon atom to which they are attached are C=N—Ac;

A compound according to formula I, II, III, or IV wherein A and B taken together with the carbon to which they are attached are C=O and X and Y taken together with the carbon atom to which they are attached are C=N—$R_1$;

A compound according to formula I, II, III, or IV wherein A and B taken together with the carbon to which they are attached are C=O, X and Y taken together with the carbon atom to which they are attached are C=N—$R_1$, and W is N(CH$_3$)$_2$;

A compound according to formula I, II, III, or IV wherein A and B taken together with the carbon to which they are attached are C=O, X and Y taken together with the carbon atom to which they are attached are C=N—Ac, and W is N(CH$_3$)$_2$; or A compound according to formula I, II, III, or IV wherein A and B taken together with the carbon atom to which they are attached are C=N—O—$R_1$, X and Y taken together with the carbon atom to which they are attached are C=N—$R_1$, L is ethyl, and W is N(CH$_3$)$_2$.

A Compound of Formula A:

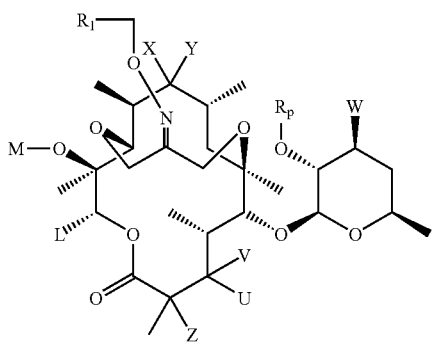

(A)

wherein M, U, V, W, X, Y, Z, $R_1$ and $R_p$ are as previously defined.

Representative compounds according to the invention are those selected from the group consisting of:

(1) compound of formula I, wherein A and B taken together with the carbon atom to which they are attached are C=N—O—CH$_2$-[5-(2-(pyrazol-1-yl)pyridine)], M is —C(O)NH$_2$, X and Y taken together with the carbon atom to which they are attached are C=N—Ac, U and V taken together with the carbon atom to which they are attached are C=O, Z is hydrogen, L is ethyl, W is N(CH$_3$)$_2$, and $R_p$ is Ac;

(2) compound of formula I, wherein A and B taken together with the carbon atom to which they are attached are C=CH$_2$, M is —C(O)NHCH$_2$CH=CH$_2$, X and Y taken together with the carbon atom to which they are attached are C=N—Ac, U and V taken together with the carbon atom to which they are attached are C=O, Z is hydrogen, L is ethyl, W is N(CH$_3$)$_2$, and $R_p$ is hydrogen;

(3) compound of formula I, wherein A and B taken together with the carbon atom to which they are attached are C=N—O—CH$_2$-[5-(2-(pyrazol-1-yl)pyridine)], M is —CH$_2$CH=CH$_2$, X and Y taken together with the carbon atom to which they are attached are C=N—Ac, U is hydrogen, V is OH, Z is hydrogen, L is ethyl, W is N(CH$_3$)$_2$, and $R_p$ is Ac;

(4) compound of formula I, wherein A and B taken together with the carbon atom to which they are attached are C=N—O—CH$_2$-[5-(2-(pyrazol-1-yl)pyridine)], M is —CH$_2$CH=CH$_2$, X and Y taken together with the carbon atom to which they are attached are C=N—Ac, U is hydrogen, V is OH, Z is hydrogen, L is ethyl, W is N(CH$_3$)$_2$, and $R_p$ is Ac;

(5) compound of formula I, wherein A and B taken together with the carbon atom to which they are attached are C=N—O—CH$_2$-[5-(2-(pyrazol-1-yl)pyridine)], M is —CH$_2$CH=CH$_2$, X and Y taken together with the carbon atom to which they are attached are C=N—Ac, U and V taken together with the carbon atom to which they are attached are C=O, Z is hydrogen, L is ethyl, W is N(CH$_3$)$_2$, and $R_p$ is Ac;

(6) compound of formula I, wherein A and B taken together with the carbon atom to which they are attached are C=N—O—CH$_2$-[5-(2-(pyrazol-1-yl)pyridine)], M is —CH$_2$CH=CH$_2$, X and Y taken together with the carbon atom to which they are attached are C=N—Ac, U and V taken together with the carbon atom to which they are attached are C=O, Z is hydrogen, L is ethyl, W is N(CH$_3$)$_2$, and $R_p$ is hydrogen;

(7) compounds of formulaes III and IV, wherein A and B taken together with the carbon atom to which they are attached are C=CH$_2$, M is hydrogen, X and Y taken together with the carbon atom to which they are attached are C=N—Ac, L is ethyl, W is N(CH$_3$)$_2$, and $R_p$ is hydrogen;

(8) compounds of formulaes III and IV, wherein A and B taken together with the carbon atom to which they are attached are C=CH—CH=CH-phenyl, M is hydrogen, X and Y taken together with the carbon atom to which they are attached are C=N—Ac, L is ethyl, W is N(CH$_3$)$_2$, and $R_p$ is Ac;

(9) compounds of formula III and IV, wherein A and B taken together with the carbon atom to which they are attached are C=CH—CH=CH-phenyl, M is hydrogen, X and Y taken together with the carbon atom to which they are attached are C=N—Ac, W is N(CH$_3$)$_2$, and $R_p$ is hydrogen;

(10) compounds of formula III, wherein A is OH, B is CH$_2$OH, M is hydrogen, X and Y taken together with the carbon atom to which they are attached are C=N—Ac, L is ethyl, W is N(CH$_3$)$_2$ and $R_p$=Ac;

(11) compounds of formula III, wherein A is OH, B is $CH_2OH$, M is hydrogen, X and Y taken together with the carbon atom to which they are attached are C=N—Ac, L is ethyl, W is $N(CH_3)_2$ and M and $R_p$ are hydrogen;

(12) compounds of formula II, wherein A, V, and $R_{21}$ are OH, B is $CH_2OH$, M and U are hydrogen, X and Y taken together with the carbon atom to which they are attached are C=N—Ac, L is ethyl, W is $N(CH_3)_2$, $R_{20}$ is methyl, and $R_p$=Ac;

(13) compound of formula I, wherein A and B taken together with the carbon atom to which they are attached are C=$CH_2$, M is —C(O)N($CH_2CH=CH_2$)($CONHCH_2CH=CH_2$), X and Y taken together with the carbon atom to which they are attached are C=N—Ac, U and V taken together with the carbon atom to which they are attached are C=O, Z is F, L is ethyl, W is $N(CH_3)_2$, and $R_p$ is Ac;

(14) compound of formula I, wherein A and B taken together with the carbon atom to which they are attached are C=$CH_2$, M is —C(O)N($CH_2CH=CH_2$)($CONHCH_2CH=CH_2$), X and Y taken together with the carbon atom to which they are attached are C=O, U and V taken together with the carbon atom to which they are attached are C=O, Z is F, L is ethyl, W is $N(CH_3)_2$, and $R_p$ is hydrogen;

(15) compound of formula II, wherein A and B taken together with the carbon atom to which they are attached are C=$CH_2$, X and Y taken together with the carbon atom to which they are attached are C=NAc, U and V taken together with the carbon atom to which they are attached are C=O, M=$R_{20}$=H, $R_{21}$=$CH_2OH$, L is ethyl, W is $N(CH_3)_2$, and $R_p$=Ac;

(16) compound of formula II, wherein A and B taken together with the carbon atom to which they are attached are C=$CH_2$, X and Y taken together with the carbon atom to which they are attached are C=NAc, U and V taken together with the carbon atom to which they are attached are C=O, M=$R_{20}$=H, $R_{21}$=$CH_2OCH_3$, L is ethyl, W is $N(CH_3)_2$, and $R_p$ is hydrogen;

(17) compound of formula II, wherein A and B taken together with the carbon atom to which they are attached are C=$CH_2$, X and Y taken together with the carbon atom to which they are attached are C=NAc, U and V taken together with the carbon atom to which they are attached are C=O, M=$R_{20}$=H, $R_{21}$=$CH_2$—NH—O—$CH_2$-[5-(2-(pyrazol-1-yl)pyridine)], L is ethyl, W is $N(CH_3)_2$, and $R_p$ is hydrogen;

(18) compound of formula II, wherein A and B taken together with the carbon atom to which they are attached are C=$CH_2$, X and Y taken together with the carbon atom to which they are attached are C=NAc, U and V taken together with the carbon atom to which they are attached are C=O, M=$R_{20}$=$R_{21}$=H, L is ethyl, W is $N(CH_3)_2$, and $R_p$ is hydrogen;

(19) compound of formula II, wherein A and B taken together with the carbon atom to which they are attached are C=N—O—$CH_2$-[5-(2-(pyrazol-1-yl)pyridine)], X and Y taken together with the carbon atom to which they are attached are C=NAc, U and V taken together with the carbon atom to which they are attached are C=O, M=$R_{20}$=H, $R_{21}$=$CH_2OH$, L is ethyl, W is $N(CH_3)_2$, and $R_p$=Ac;

(20) compound of formula II, wherein A and B taken together with the carbon atom to which they are attached are C=N—O—$CH_2$-[5-(2-(pyrazol-1-yl)pyridine)], X and Y taken together with the carbon atom to which they are attached are C=NAc, U and V taken together with the carbon atom to which they are attached are C=O, M=$R_{20}$=$R_{21}$=H, L is ethyl, W is $N(CH_3)_2$, and $R_p$=Ac;

(21) compound of formula II, wherein A and B taken together with the carbon atom to which they are attached are C=N—O—$CH_2$-[5-(2-(pyrazol-1-yl)pyridine)], X and Y taken together with the carbon atom to which they are attached are C=NAc, U and V taken together with the carbon atom to which they are attached are C=O, M=$R_{20}$=$R_{21}$=$R_p$=H, L is ethyl, and W is $N(CH_3)_2$;

(22) compound of formula II, wherein A and B taken together with the carbon atom to which they are attached are C=N—O—$CH_2$-[5-(2-(pyrazol-1-yl)pyridine)], X and Y taken together with the carbon atom to which they are attached are C=NAc, U and V taken together with the carbon atom to which they are attached are C=O, M=$R_{20}$=H, $R_{21}$=$CH_2CH=CH_2$, L is ethyl, W is $N(CH_3)_2$, and $R_p$=Ac;

(23) compound of formula II, wherein A and B taken together with the carbon atom to which they are attached are C=N—O—$CH_2$-[5-(2-(pyrazol-1-yl)pyridine)], X and Y taken together with the carbon atom to which they are attached are C=NAc, U and V taken together with the carbon atom to which they are attached are C=O, M=$R_{20}$=H, $R_{21}$=$CH_2CH=CH_2$, L is ethyl, W is $N(CH_3)_2$, and $R_p$ is hydrogen;

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

Yet a further embodiment of the present invention is a pharmaceutical composition comprising any single compound delineated herein in combination with one or more antibiotics known in the art (such as penicillin, amoxicillin, azithromycin, erythromycin, ciproflaxin, telithromycin, cethromycin, and the like) or a pharmaceutically acceptable salt, ester, or prodrug thereof, with a pharmaceutically acceptable carrier or excipient.

Yet an additional aspect of the present invention relates to a method of treating a subject (e.g., mammal, human, horse, dog, cat, fish) having bacterial infection or disease or disease symptom related to having a bacterial infection (including diseases delineated herein). The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Also within the scope of this invention is a packaged product. The packaged product includes a container, one of the aforementioned compounds in the container, and a legend (e.g., a label or an insert) associated with the container and indicating administration of the compound for treating a disorder associated with bacterial infection, including the diseases delineated herein.

Definitions

Listed below are definitions of various terms used to describe this invention. These definitions apply to the terms as they are used throughout this specification and claims, unless otherwise limited in specific instances, either individually or as part of a larger group.

An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The terms "$C_1$-$C_3$ alkyl," "$C_1$-$C_6$ alkyl," or "$C_1$-$C_{12}$ alkyl," as used herein, refer to saturated, straight- or branched-chain hydrocarbon radicals containing between one and three, one and twelve, or one and six carbon atoms, respectively. Examples of $C_1$-$C_3$ alkyl radicals include methyl, ethyl, propyl and isopropyl radicals; examples of $C_1$-$C_6$ alkyl radicals include, but are not limited to, methyl, ethyl, propyl, propyl, butyl, pentyl, and hexyl radicals; and examples of $C_1$-$C_{12}$ alkyl radicals include, but are not limited to, ethyl, propyl, propyl, hexyl, heptyl, octyl, nonyl, decyl, undecyl, dodecyl radicals and the like.

The term "substituted alkyl," as used herein, refers to an alkyl, such as a $C_1$-$C_{12}$ alkyl or $C_1$-$C_6$ alkyl group, substituted by one, two, three or more aliphatic substituents.

Suitable aliphatic or aromatic substituents include, but are not limited to, —F, —Cl, —Br, —I, —OH, protected hydroxy, aliphatic ethers, aromatic ethers, oxo, —$NO_2$, —CN, —$C_1$-$C_{12}$-alkyl optionally substituted with halogen (such as perhaloalkyls), $C_2$-$C_{12}$-alkenyl optionally substituted with halogen, —$C_2$-$C_{12}$-alkynyl optionally substituted with halogen, —$NH_2$, protected amino, —NH —$C_1$-$C_{12}$-alkyl, —NH —$C_2$-$C_{12}$-alkenyl, —NH —$C_2$-$C_{12}$-alkynyl, —NH —$C_3$-$C_{12}$-cycloalkyl, —NH -aryl, —NH -heteroaryl, —NH -heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_2$-alkynyl, —CONH—$C_3$-$C_{12}$-cycloalkyl, —CONH-aryl, —CONH-heteroaryl, —CONH-heterocycloalkyl, —$CO_2$—$C_1$-$C_{12}$-alkyl, —$CO_2$—$C_2$-$C_{12}$-alkenyl, —$CO_2$—$C_2$-$C_{12}$-alkynyl, —$CO_2$—$C_3$-$C_{12}$-cycloalkyl, —$CO_2$-aryl, —$CO_2$-heteroaryl, —$CO_2$-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH— aryl, —OCONH— heteroaryl, —OCONH— heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$— aryl, —$NHCO_2$-heteroaryl, —$NHCO_2$— heterocycloalkyl, —NHC(O)$NH_2$, NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkynyl, —$SO_2$NH—$C_3$-$C_{12}$-cycloalkyl, —$SO_2$NH— aryl, —$SO_2$NH— heteroaryl, —$SO_2$NH— heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_2$-alkenyl, —S—$C_2$-$C_{12}$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls and the like can be further substituted.

The terms "$C_2$-$C_{12}$ alkenyl" or "$C_2$-$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "$C_2$-$C_{12}$ alkenyl" or "$C_2$-$C_6$ alkenyl" group as previously defined, substituted by one, two, three or more aliphatic substituents.

The terms "$C_2$-$C_{12}$ alkynyl" or "$C_2$-$C_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "$C_2$-$C_{12}$ alkynyl" or "$C_2$-$C_6$ alkynyl" group as previously defined, substituted by one, two, three or more aliphatic substituents.

The term "$C_1$-$C_6$ alkoxy," as used herein, refers to a $C_1$-$C_6$ alkyl group, as previously defined, attached to the parent molecular moiety through an oxygen atom. Examples of $C_1$-$C_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen," as used herein, refer to an atom selected from fluorine, chlorine, bromine and iodine.

The terms "aryl" or "aromatic," as used herein, refer to a mono- or bicyclic carbocyclic ring system having one or two aromatic rings including, but not limited to, phenyl, naphthyl, tetrahydronaphthyl, indanyl, idenyl and the like.

The terms "substituted aryl" or "substituted aromatic," as used herein, refer to an aryl group, as previously defined, substituted by one, two, three or more aromatic substituents.

The term "arylalkyl," as used herein, refers to an aryl group attached to the parent compound via a $C_1$-$C_3$ alkyl or $C_1$-$C_6$ alkyl residue. Examples include, but are not limited to, benzyl, phenethyl and the like.

The term "substituted arylalkyl," as used herein, refers to an arylalkyl group, as previously defined, substituted by one, two, three or more aromatic substituents.

The terms "heteroaryl" or "heteroaromatic," as used herein, refers to a mono-, bi-, or tri-cyclic aromatic radical or ring having from five to ten ring atoms of which at least one ring atom is selected from S, O and N; zero, one, two, three or more ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, tetrazolyl and the like. The heteroaromatic ring may be bonded to the chemical structure through a carbon or hetero atom.

The terms "substituted heteroaryl" or "substituted heteroaromatic," as used herein, refer to a heteroaryl group as previously defined, substituted by one, two, three or four aromatic substituents.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1]heptyl, and bicyclo [2.2.2] octyl.

The term "substituted alicyclic" group as previously defined, substituted by one, two, three or more aliphatic substituents.

The terms "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloakyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl, and the like.

The term "substituted heterocyclic," as used herein, refers to a heterocyclic group, as previously defined, substituted by one, two, three or more aliphatic substituents.

The term "heteroarylalkyl," as used herein, refers to a heteroaryl group attached to the parent compound via a $C_1$-$C_3$ alkyl or $C_1$-$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more aromatic substituents.

The term "$C_1$-$C_3$-alkylamino," as used herein, refers to one or two $C_1$-$C_3$-alkyl groups, as previously defined, attached to the parent molecular moiety through a nitrogen atom. Examples of $C_1$-$C_3$-alkylamino include, but are not limited to, methylamino, dimethylamino, ethylamino, diethylamino, and propylamino.

The term "alkylamino" refers to a group having the structure —NH($C_1$-$C_{12}$ alkyl) where $C_1$-$C_{12}$ alkyl is as previously defined.

The term "dialkylamino" refers to a group having the structure —N($C_1$-$C_{12}$ alkyl) ($C_1$-$C_{12}$ alkyl), where $C_1$-$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$-$C_{12}$ alkyl) or —C(O)N($C_1$-$C_{12}$ alkyl) ($C_1$-$C_{12}$ alkyl), —C(O)NH$_2$, —NHC(O)($C_1$-$C_{12}$ alkyl), —N($C_1$-$C_{12}$ alkyl)C(O)($C_1$-$C_{12}$ alkyl) and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)$C_6H_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protogenic organic solvent" or "protic solvent," as used herein, refers to a solvent that tends to provide protons, such as an alcohol, for example, methanol, ethanol, propanol, isopropanol, butanol, t-butanol, water and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating bacterial infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, sinusitus, bronchitis, tonsillitis, cystic fibrosis (CF) and mastoiditis related to infection by *Streptococcus pneumoniae, Haemophilus influenzae, Moraxella catarrhalis, Staphylococcus aureus, Peptostreptococcus* spp. or *Pseudomonas* spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *S. pyogenes, S. agalactiae*, Streptococcal groups C-F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Nesseria gonorrheae*; toxin diseases related to infection by *S. aureus* (food poisoning and Toxic shock syndrome), or Groups A, S. and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; tuberculosis disease related to infection by *Mycobacterium tuberculosis*; gastroenteritis related to infection by *Campylobacter jejuni*; intestinal protozoa related to infection by *Cryptosporidium* spp. odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium* acne; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica., P. multocida, Mycoplasma bovis*, or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium*, or *Enterococcus* spp.; swine respiratory disease related to infection by *A. pleuropneumoniae., P. multocida*, or *Mycoplasma* spp.; swine enteric disease related to infection by *E. coli*, Lawsonia intracellularis, *Salmonella* spp., or Serpulina hyodyisinteriae; cow footrot related to infection by *Fusobacterium* spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. *Staphylococcus* or *P. multocida*; and dental or mouth infections in dogs and oats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., and *Trichomonas* spp. or *Prevotella* spp. Other bacterial infections and protozoa infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds are tested for in vitro antibacterial activity by a micro-dilution method. Minimal Inhibitory Concentration (MIC) is determined in 96 well microtiter plates utilizing the appropriate Mueller Hinton Broth medium (CAMHB) for the observed bacterial isolates. Antimicrobial agents are serially diluted (2-fold) in DMSO to produce a concentration range from about 64 µg/ml to about 0.03 µg/ml. The diluted compounds (2 µl/well) are then transferred into sterile, uninoculated CAMHB (0.2 mL) by use of a 96 fixed tip-pipetting station. The inoculum for each bacterial strain is standardized to $5 \times 10^5$ CFU/mL by optical comparison to a 0.5 McFarland turbidity standard. The plates are inoculated with 10 µl/well of adjusted bacterial inoculum. The 96 well plates are covered and incubated at 35+/−2° C. for 24 hours in ambient air environment. Following incubation, plate wells are visually examined by Optical Density measurement for the presence of growth (turbidity). The lowest concentration of an antimicrobial agent at which no visible growth occurs is defined as the MIC. The compounds of the invention generally demonstrated an MIC in the range from about 64 µg/ml to about 0.03 µg/ml.

All in vitro testing follows the guidelines described in the Approved Standards M7-A4 protocol, published by the National Committee for Clinical Laboratory Standards (NCCLS).

The invention further provides compositions and methods of treating patients suffering from an inflammatory condition comprising administering to a patient in need thereof, a therapeutically effective amount of at least one compound of the invention. Specific examples of inflammatory conditions treatable according to the invention include, but are not limited to, scleritis; epi-scleritis; allergic conjunctivitis; pulmonary inflammatory diseases, particularly CF, asthma, chronic obstructive pulmonary disease (COPD), allergic bronchopulmonary aspergillosis (ABPA), and sarcoidosis; procto-sigmoiditis; allergic rhinitis; arthritis; tendonitis; apthous stomatitis; and inflammatory bowel disease.

The invention further provides compositions and methods for i) prophylactic treatment of those patients susceptible to the symptoms CF including pulmonary infection and inflammation associated with CF, ii) treatment at the initial onset of symptoms of pulmonary infection and inflammation associated with CF, and iii) treatment of ongoing or relapsing symptoms of infection and inflammation associated with CF. In accordance with the invention a compound of the invention, is administered to a patient in need of treatment for CF, in amount sufficient to prevent, diminish or eradicate symptoms of CF including chronic pulmonary inflammation and infection.

Pharmaceutical Compositions.

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, all of which are incorporated herein by reference). A discussion of pulmonary delivery of antibiotics is also found in U.S. Pat. No. 6,014,969, incorporated herein by reference.

According to the methods of treatment of the present invention, bacterial infections, cystic fibrosis and inflammatory conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically exipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5-1000 mg, preferably 20-100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are:
Ac for acetyl;
AIBN for azobisisobutyronitrile;
$Bu_3SnH$ for tributyltin hydride;
CDI for carbonyldiimidazole;
dba for dibenzylidene acetone;
dppb for diphenylphosphino butane;
DBU for 1,8-diazabicyclo[5.4.0]undec-7-ene;
DEAD for diethylazodicarboxylate;
DMAP for dimethylaminopyridine;
DMF for dimethyl formamide;
DPPA for diphenylphosphoryl azide;
EtOAc for ethyl acetate;
MeOH for methanol;
Ms for mesylate or $O-SO_2-CF_3$;
$NaN(TMS)_2$ for sodium bis(trimethylsilyl)amide;
NMMO for N-methylmorpholine N-oxide;
TEA for triethylamine;
THF for tetrahydrofuran;
TPP or $PPh_3$ for triphenylphosphine;
MOM for methoxymethyl;
Boc for t-butoxycarbonyl;
Bz for benzoyl;
Bn for benzyl;
Ph for phenyl;
POPd for dihydrogen dichlorobis(di-tert-butylphosphinito-κP)palladate(II);
TBS for tert-butyl dimethylsilyl; or
TMS for trimethylsilyl.

Synthetic Methods

The compounds and processes of the present invention will be better understood in connection with the following synthetic schemes illustrating the methods by which the compounds of the invention may be prepared.

A preferred intermediate for the preparation of the compounds of the present invention are compounds of formula (1-1):

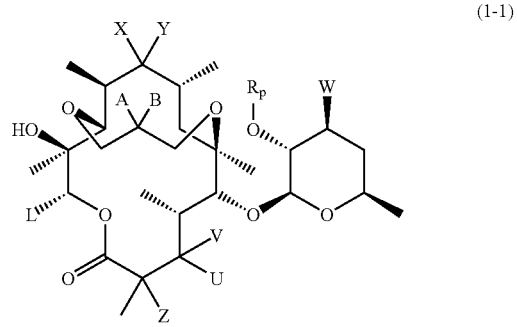

(1-1)

Compounds of formula (1-1), as well as methods of preparing such compounds, are described in U.S. application Ser. Nos. 10/429,485 and 10/436,602.

Scheme 1
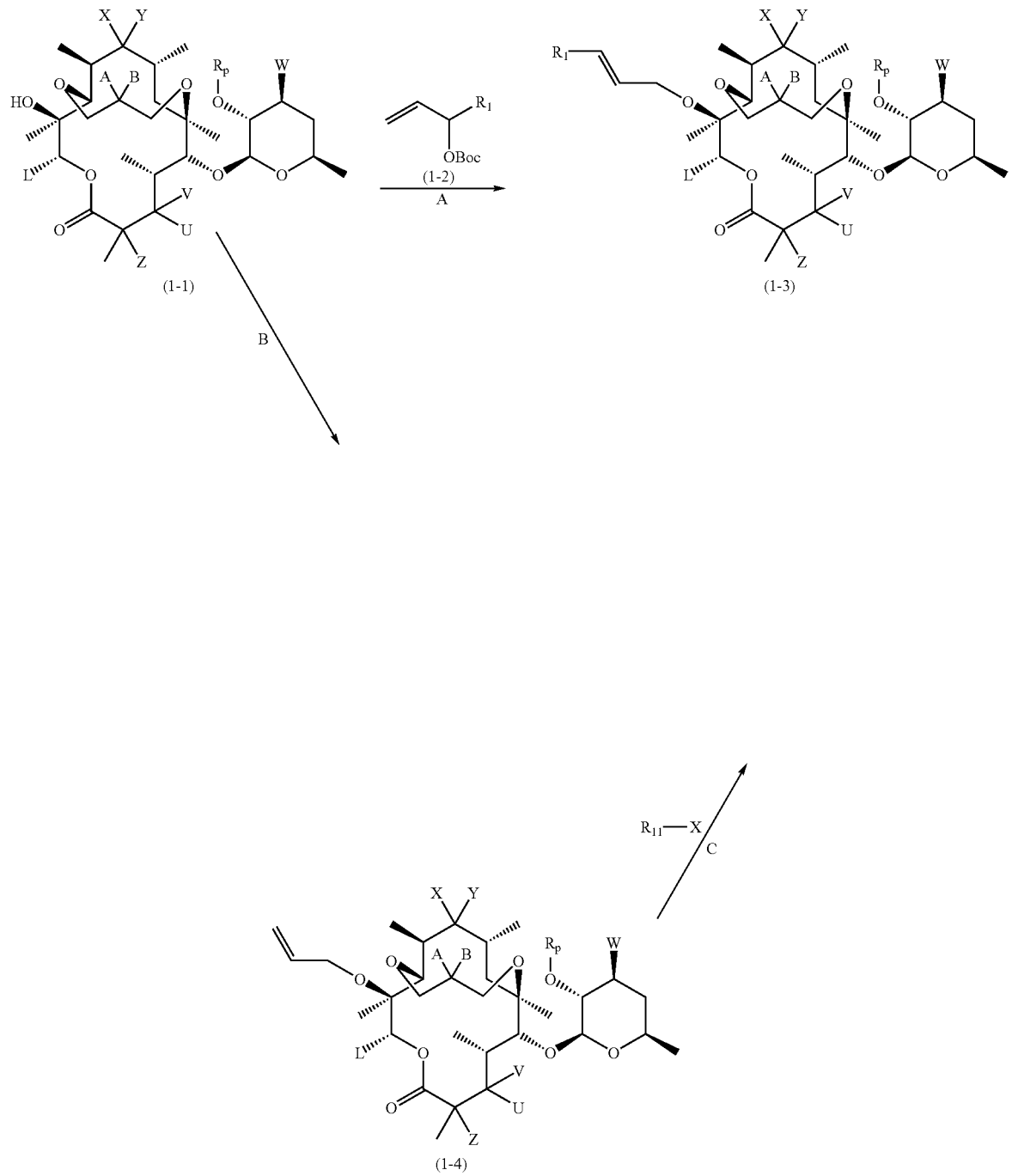

Scheme 1 illustrates a process of preparing compounds of the present invention, comprising the step of treating a compound of formula (1-1) with a tert-butyl allyl carbonate (1-2) in the presence of a palladium catalyst [Pd(0) or Pd(II)] and an additive, in aprotic solvents from about room temperature to about 100° C. to provide a compound of formula (1-4) (see (a) Trost, B. M. *Angew. Chem. Int. Ed. Eng.* 1989, 28, 11179; (b) Heck, Palladium Reagents in Organic Synthesis, Academic Press: New York, 1985, Chapter 1; (c) Tsuji, *Tetrahedron Lett.* 1992, 33, 2987). Compound (1-4) may further be derivatized through treatment with an aryl halide or aryl triflate in the presence of a palladium catalyst [Pd(0) or Pd(II)] with a phosphorus ligand and a base such as TEA or $K_2CO_3$ to provide compound (1-3) (see (a) Heck, Palladium Reagents in Organic Synthesis, Academic Press: New York, 1985, Chapter 1; (b) Sonogashira, Comprehensive Organic Synthesis, Volume 3, Chapters 2, 4; (c) Sonogashira, *Synthesis* 1977, 777).

Alternatively, compound (1-3) can be obtained by treating compound (1-1) with substituted tert-butyl allyl carbonate of formula (1-2), wherein $R_1$ is as previously defined, in the presence of a palladium catalyst and a phosphine additive. Compounds of formulas (1-3) or (1-4) may optionally be hydrogenated with Palladium on carbon, Palladium black, Platinum oxide or the like under 1-4 atm pressure of hydrogen in a solvent such as methanol, ethanol, ethyl acetate at a temperature from about 0° C. to about 50° C. for less than 36 hours to provide the corresponding saturated compounds.

Scheme 2

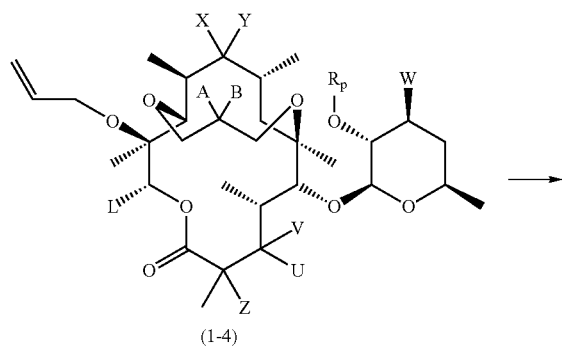

(1-4)

-continued

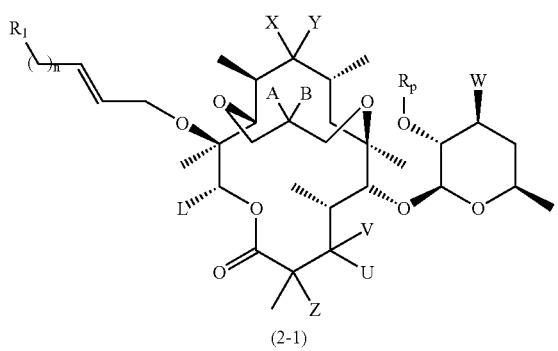

(2-1)

Scheme 2 illustrates cross metathesis reaction of a compound of formula (1-4) with alkenyl derivatives of formula $CH_2=CH-(CH_2)_n-R$, using ruthenium catalysts in an aprotic solvent such as methylene chloride, THF, chloroform, DMF, or acetonitrile, at from 0° C. to 80° C. for less than 48 hours to produce compound (2-1) (see (a) *J. Org. Chem.* 2000, 65, 2204-2207; (b) Reviews: *Synlett.* 1999, 2, 267; (c) Reviews: Ivin, K. J.; Mol, J. C. *Olefin Metathesis and Metathesis Polymerization*, 2$^{nd}$ ed.; Academic Press: New York, 1997; (d) *J. Org. Chem.* 1999, 64, 4798-4816; (e) *Angew. Chem., Int. Ed. Engl.* 1997, 36, 2036-2056; (f) *Tetrahedron* 1998, 54, 4413-4450). Compound (2-1) may optionally be hydrogenated as described in Scheme 1.

Scheme 3

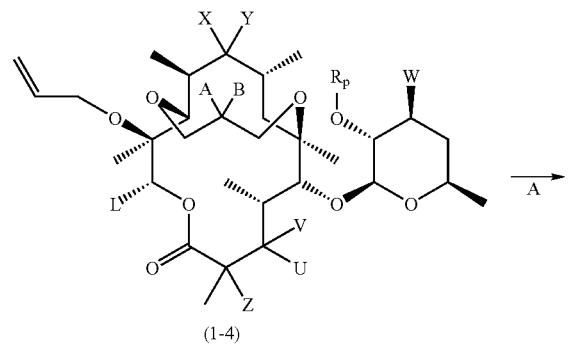

(1-4)

A →

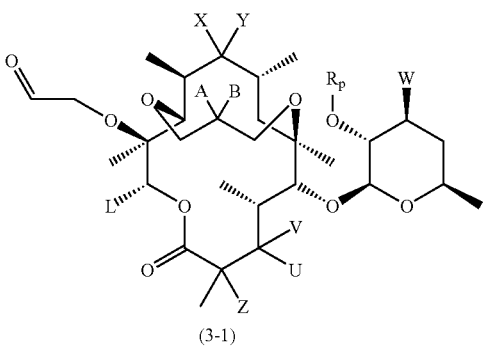

(3-1)

↙ B

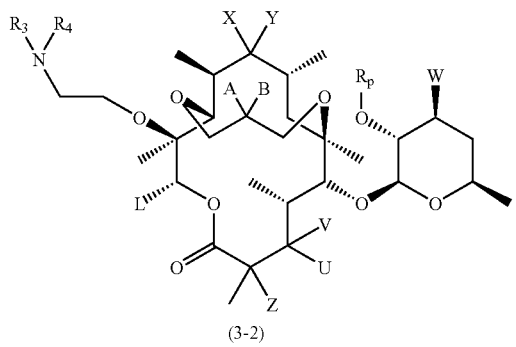

(3-2)

As illustrated in Scheme 3, Step A allyl compounds of formula (1-4) can be oxidatively cleaved to form an aldehyde compound of formula (3-1). Oxidative cleavage may be performed by, for example, ozonolysis or by treatment with an oxidant followed by cleaving reagent. Ozonolysis may be achieved by treating the alkene of a compound of formula (1-4) with ozone followed by decomposition of the ozonide with the appropriate reducing agent. Suitable reducing agents for this process include, but are not limited to, dimethyl sulfide, zinc, trivalent phosphorous compounds, sodium sulfite, and the like. The reaction is typically carried out in an inert solvent such as, but not limited to, methanol, ethanol, ethyl acetate, glacial acetic acid, chloroform, methylene chloride or hexanes or mixtures thereof, preferably methanol, preferably at −78° to −20° C. Preferred reducing agents include, but are not limited to, triphenylphosphine, trimethyl phosphite, thiourea, and dimethyl sulfide, preferably triphenylphosphine. A more thorough discussion of ozonolysis and the conditions there for can be found in J. March "Advanced Organic Chemistry" 4$^{th}$ ed., Wiley & Son, Inc, 1992.

An alternative method for the preparation of a compound of formula (3-1) involves dihydroxylation of a compound of formula (1-4) by an oxidant followed by treatment with a cleaving reagent. The glycol is first prepared by reacting alkene with an oxidant. Suitable oxidants for the present process include, but are not limited to, permanganate ion and osmium tetroxide. The process may utilize stochiometric amounts of osmium tetroxide, or, if in the presence of an additional oxidant such as hydrogen peroxide, tert-butyl hydroperoxide, N-methylmorpholine-N-oxide, or barium chlorate only catalytic amounts of osmium tetroxide are necessary. Dihydroxylation reactions can be carried out in a variety of solvents including: 1,4-dioxane, tetrahydrofuran, tert-butanol and diethyl ether, preferably at a temperature of between −15° C. and 15° C.

The resulting glycol can be cleaved by a variety of cleaving reagents including, but not limited to, periodic acid, lead tetraacetate, manganesedioxide, potassium permanganate, sodium metaperiodate, and N-iodosuccinamide. Preferably the cleavage reagent is sodium periodate, the solvent is preferably a mixture of ethanol, methanol or 1,4-dioxane and water at a temperature of between 0° to 25° C.

As illustrated in Scheme 3, Step B, compounds of formula (3-1) may undergo reductive amination by treatment with primary or secondary amines of the formula $HN(R_3)(R_4)$, where $R_3$ and $R_4$ are as previously defined, optionally in the presence in an acid, followed by treatment with a reducing agent, such as $NaCNBH_3$.

Scheme 4

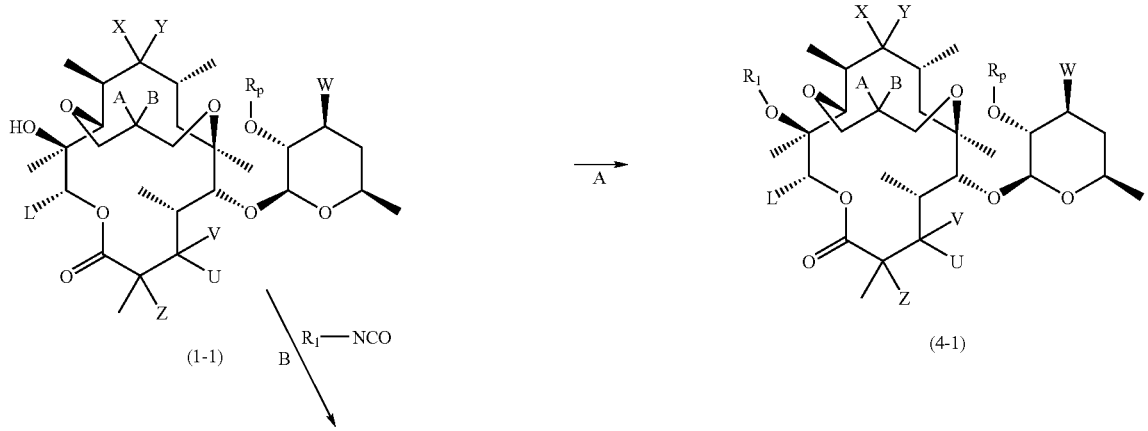

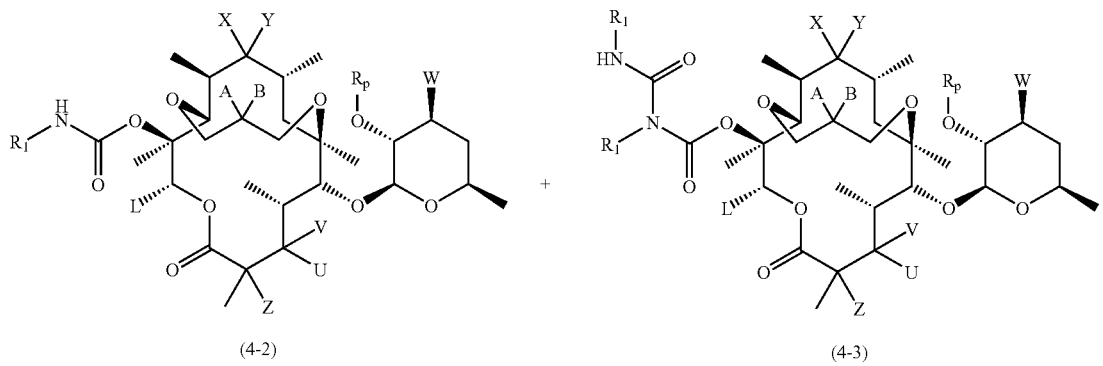

(4-2)     (4-3)

As illustrated in Scheme 4, Compound (1-1) can be treated with an alkylating agent of the formula $R_1$—$S(O)_3R_x$ or $R_1$—X, $R_x$ is $CF_3$— or $CH_3$—, and X is halogen. Preferred groups for the present process include, but are not limited to, propargyl halide, allyl halide, arylallyl halide, heteroarylallyl halide, or benzyl halide. The present process occurs preferably in the presence of a base such as sodium hydride, potassium hydride, potassium tert-butoxide, potassium hydroxide, KHMDS, and the like, in an aprotic solvent such as THF, DMSO, DMF, or dioxane, or mixtures thereof, at from about −20° C. to about 60° C. to provide a compound of formula (4-1). The alcohol compound can be converted to an ether by treatment with an alkylating agent including, but not limited to, alkyl halides, alkyl sulphonates, propargyl halides, allyl halides, arylallyl halides, heteroarylallyl halides, or benzyl halides, in the presence of a base such as sodium hydride, potassium hydride, potassium tert-butoxide, potassium hydroxide, or KHMDS, in an aprotic solvent such as THF, DMSO, DMF, or dioxane, or mixtures thereof at from −20° C. to 60° C.

Compounds of formula (1-1) can also be treated with an isocyanate reagent of the formula $R_1$—NCO in an aprotic solvent such as methylene chloride, ethylene chloride, THF, chloroform, DMF, or acetonitrile at a temperature of 0° C. to 50° C. for a period of less than 48 hours, to provide compound (4-2). In some instances, double addition occurs yielding compounds of formula (4-3).

All compounds described herein may be optionally deprotected to form compounds wherein $R_p$ is hydrogen.

Scheme 5

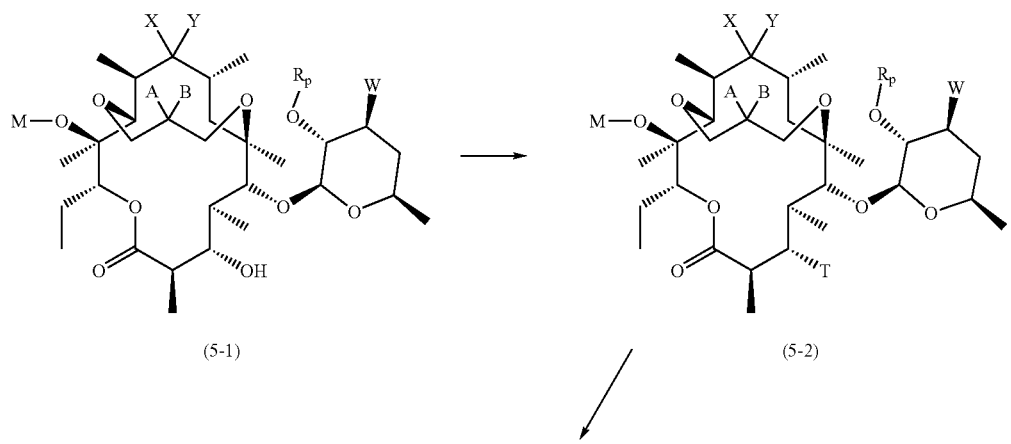

(5-1)     (5-2)

-continued

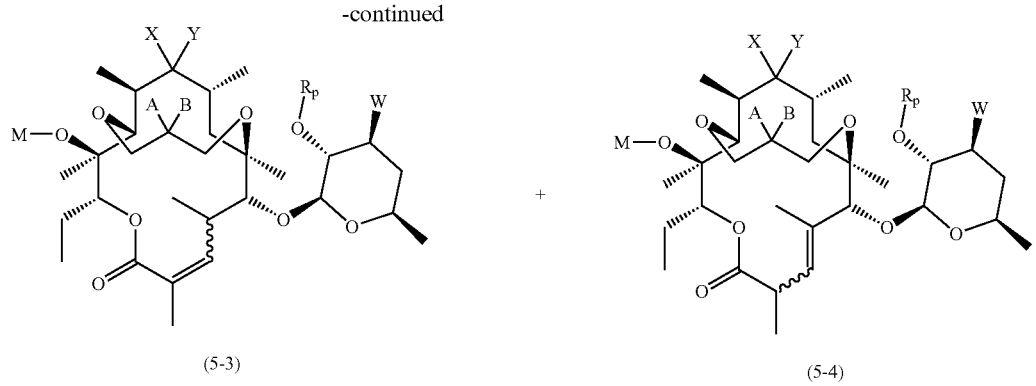

Scheme 5 illustrates the processes for the synthesis of compounds of formula (5-1) which are prepared by methods which are well known in the art via compounds of formula (1-1) Compounds of formula (1.1) are reacted with sulfonic anhydride, or sulfonyl chloride in an aprotic organic solvent such as methylene chloride, ethylene chloride, THF, chloroform or the like at a temperature from about −78° C. to about 50° C. for less than 48 hours in the presence of an amine base, such as pyridine, diethylamine, triethylamine or the like, optionally by adding a catalyst such as DMAP, imidazole or the like to provide compounds of formula (5-2) where T is a mesylate or a tosylate. Compounds of formula (5-3) and (5-4) are obtained by treating compounds of formula (5-2) with a base such as DBU, DIEA, triethylamine or the like in solvents such as acetone, DMF, DMSO at a temperature from 25° C. to 100° C. for less than 48 hours.

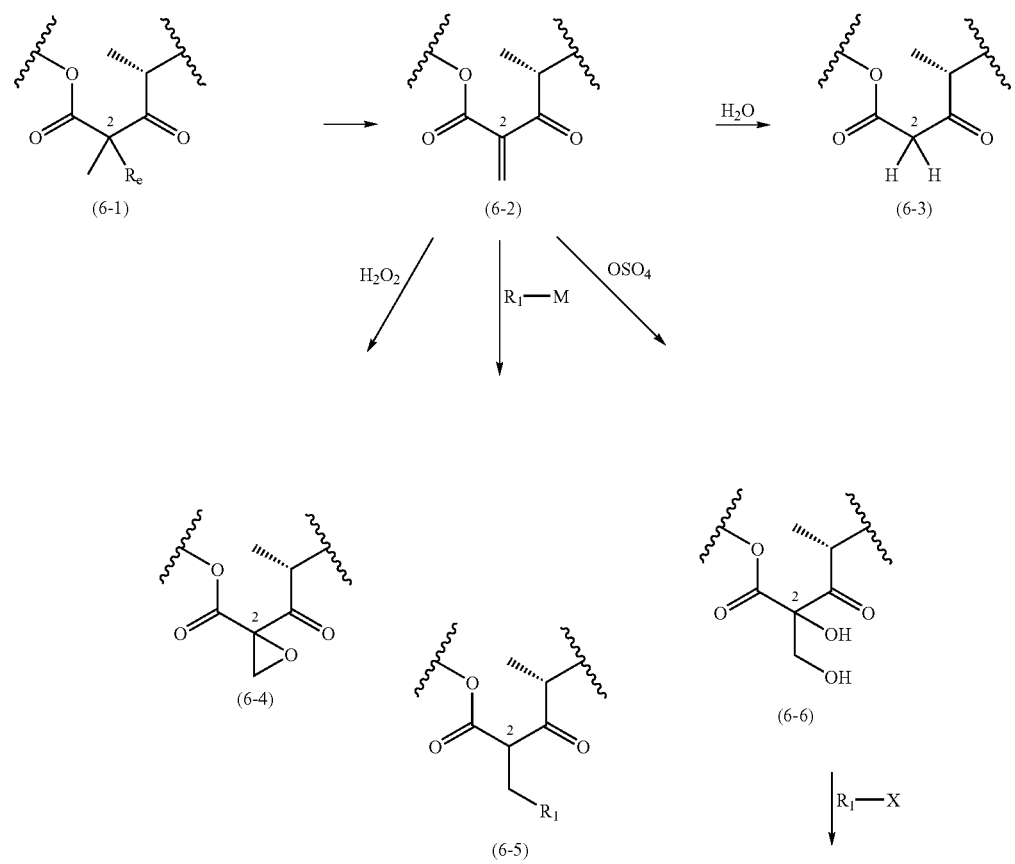

-continued

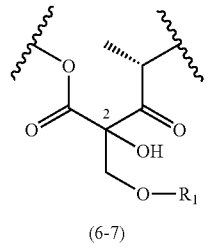

(6-7)

The 2-desmethyl compounds of the present invention may be produced from the ketolide of formula (6-1), as illustrated in Scheme 6, or derived from the 2-norerythromycin fermentation product. Compounds of formula (6-1), where $R_e$ is selected from hydroxy, halide, sulfone, sulfoxide, sulfide, or selenide, are produced through the treatment with the appropriate electrophilic reagent. The C2-electrophile of compound of formula (6-1) is then eliminated to form compounds of formula (6-2). Compounds of formula (6-2) may subsequently manipulated to form compounds of formulas (6-3) through (6-7) as illustrated in Scheme 6 via methods described in U.S. Pat. No. 6,569,836.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of formula I, wherein A and B taken together with the carbon atom to which they are attached are C=N—O—CH$_2$-[5-(2-(pyrazol-1-yl)pyridine)], M is —C(O)NH$_2$, X and Y taken together with the carbon atom to which they are attached are C=N—Ac, U and V taken together with the carbon atom to which they are attached are C=O, Z is hydrogen, L is ethyl, W is N(CH$_3$)$_2$, and $R_p$ is Ac.

Step 1a. To a solution of compound of formula (1-1, wherein A and B taken together with the carbon atom to which they are attached are C=N—O—CH$_2$-pyridyl-pyrazolyl, X and Y taken together with the carbon atom to which they are attached are C=N—Ac, U and V taken together with the carbon atom to which they are attached are C=O, M and Z are hydrogen, L is ethyl, W is N(CH$_3$)$_2$, and $R_p$ is Ac) (prepared according to U.S. application Ser. Nos. 10/429,485 and 10/436,60) (180 mg, 0.22 mmol) in THF (3 mL) was added trichloroacetyl isocyanate (393 μL, 3.3 mmol) and CuI (catalytic amount) at room temperature. The mixture was stirred for 30 mins, then diluted with EtOAc and washed with saturated NaHCO$_3$ solution and brine. The organic solution was dried (Na$_2$SO$_4$), filtered and concentrated under reduced pressure. The residue was purified by chromatography (silica, hexane:acetone 1:1 and 2:3) to give 170 mg (~78%) of the desired compound.

MS (ESI) m/z=1070 (M+H)$^+$.

Step 1b. A solution of the compound from step 1a in 2N NH$_3$-methanol was heated at 45° C. for 1.5 hours, evaporated and the residue was purified by column chromatography (MeOH: CH$_2$Cl$_2$ 2:98 and 4:96) to give 110 mg the title compound as a E/Z mixture. HPLC purification gave 35 mg pure E isomer.

(ESI) m/z=884 (M+H)$^+$.

Example 2

Compound of formula I, wherein A and B taken together with the carbon atom to which they are attached are C=CH$_2$, M is —C(O)NHCH$_2$CH=CH$_2$, X and Y taken together with the carbon atom to which they are attached are C=N—Ac, U and V taken together with the carbon atom to which they are attached are C=O, Z is hydrogen, L is ethyl, W is N(CH$_3$)$_2$, and $R_p$ is hydrogen.

Step 2a. To a solution of compound of formula (1-1, wherein A and B taken together with the carbon atom to which they are attached are C=CH$_2$, X and Y taken together with the carbon atom to which they are attached are C=N—Ac, U and V taken together with the carbon atom to which they are attached are C=O, M and Z are hydrogen, L is ethyl, W is N(CH$_3$)$_2$, and $R_p$ is Ac) (prepared according to U.S. application Ser. Nos. 10/429,485 and 10/436,60) (180 mg, 0.25 mmol) in THF (2.5 mL) was added allyl isocyanate (126 μL, 1.43 mmol) and CuI (catalytic amount) at room temperature. The mixture was stirred for about 18 hrs, then another 50 μL of the isocyanate was added. The mixture was stirred for another 22 hrs at room temperature, then was diluted with CH$_2$Cl$_2$ and washed with saturated NaHCO$_3$ solution. The organic solution was dried (Na$_2$SO$_4$), filtered and concentrated under reduced pressure. The residue was purified by chromatography (silica, hexane:acetone 4:1) to give 35 mg of pure the desired product.

MS (ESI) m/z=792 (M+H)$^+$.

Step 2b. A solution of the compound from step 2a in methanol is stirred at room temperature for about 16 hours, evaporated give the title compound.

MS (ESI) m/z=750 (M+H)$^+$.

Example 3

Compound of formula I, wherein A and B taken together with the carbon atom to which they are attached are C=N—O—CH$_2$-[5-(2-(pyrazol-1-yl)pyridine)], M is —CH$_2$CH=CH$_2$, X and Y taken together with the carbon atom to which they are attached are C=N—Ac, U is hydrogen, V is OTMS, Z is hydrogen, L is ethyl, W is N(CH$_3$)$_2$, and R$_p$ is Ac.

Step 3a. To a solution of compound of formula (1-1, wherein A and B taken together with the carbon atom to which they are attached are C=N—O—CH$_2$-pyridyl-pyrazolyl, X and Y taken together with the carbon atom to which they are attached are C=N—Ac, U and V taken together with the carbon atom to which they are attached are C=O, M and Z are hydrogen, L is ethyl, W is N(CH$_3$)$_2$, and R$_p$ is Ac) (prepared according to U.S. application Ser. Nos. 10/429,485 and 10/436,60) (4.4 g, 5 mmol) and imidazole (1.36 g, 20 mmol) in 10 mL DMF was added TMSCl (1.9 mL) 15 mmol) at room temperature. The mixture was stirred at room temperature for 2 hours and quenched with saturated NaHCO$_3$ (50 mL). The mixture was extracted with ethyl acetate (60 ml) and washed with brine (50 mL×2) and the dried over Na$_2$SO$_4$. The solvent was removed and the residue is purified on silica gel column (Hexane:acetone=3:1) to give 3.8 g of desired compound.

MS (ESI) m/z=957.68.

Step 3b. A solution of the compound from Step 3a (1.92 g, 2 mmol), allyl Boc (632 mg, 4 mmol), Pd$_2$(dba)$_3$ (91.6 mg, 0.1 mmol) and dppb (85 mg, 0.2 mmol) in 10 mL THF was degassed and heated to reflux. The mixture was refluxed for 5 hours and concentrated. The residue was purified via a silica gel column (Hexane:acetone=3:1) to give the title compound (1.6 g).

MS (ESI) m/z=997.69.

Example 4

Compound of formula I, wherein A and B taken together with the carbon atom to which they are attached are C=N—O—CH$_2$-[5-(2-(pyrazol-1-yl)pyridine)]M is —CH$_2$CH=CH$_2$, X and Y taken together with the carbon atom to which they are attached are C=N—Ac, U is hydrogen V is OH, Z is hydrogen, L is ethyl, W is N(CH$_3$)$_2$, and R$_p$ is Ac.

To a solution prepared in Example 3 ((1.5 g) in 15 mL of THF) was added TBAF (1M in THF, 2 mL) and the mixture was stirred at room temperature for 2 hours. The solvent was removed and the residue was purified on silica gel column to give the title compound (1.4 g).

MS (ESI) m/z=925.65.

Example 5

Compound of formula I, wherein A and B taken together with the carbon atom to which they are attached are C=N—O—CH$_2$-[5-(2-(pyrazol-1-yl)pyridine)], M is —CH$_2$CH=CH$_2$, X and Y taken together with the carbon atom to which they are attached are C=N—Ac, U and V taken together with the carbon atom to which they are attached are C=O, Z is hydrogen, L is ethyl, W is N(CH$_3$)$_2$, and R$_p$ is Ac.

To a solution of the title compound from Example 4 (3.7 g, 4 mmol) in CH$_2$Cl$_2$ (20 mL) was added HOAc (0.5 mL) and Dess-Martin reagent (2.13 g, 5 mmol) at room temperature. The mixture was stirred at room temperature for 3 hours and quenched with saturated sodium thiosulfate (50 mL). The resulting quenched reaction mixture was then extracted with CH$_2$Cl$_2$ (50 ml) and washed with brine (50 mL×2). The solvent was removed and the residue was purified on silica gel column to give the title compound (3.1 g).

MS (ESI) m/z=923.45

Example 6

Compound of formula I, wherein A and B taken together with the carbon atom to which they are attached are C=N—O—CH$_2$-[5-(2-(pyrazol-1-yl)pyridine)], M is —CH$_2$CH=CH$_2$, X and Y taken together with the carbon atom to which they are attached are C=N—Ac, U and V taken together with the carbon atom to which they are attached are C=O, Z is hydrogen, L is ethyl, W is N(CH$_3$)$_2$, and R$_p$ is hydrogen.

A solution of the title compound of Example 5 (3.0 g) in 50 mL of methanol was stirred at 60° C. for 6 hours and concentrated. The residue was purified on silica gel column to give the title compound (2.8 g).

MS (ESI) m/z=881.45

Example 7

Compounds of formulaes III and IV wherein A and B taken together with the carbon atom to which they are attached are C=CH$_2$, M is hydrogen, X and Y taken together with the carbon atom to which they are attached are C=N—Ac, L is ethyl, W is N(CH$_3$)$_2$, and R$_p$ is hydrogen.

Step 7a. Into a solution of imidazole (68 mg, 1.00 mmol) in DMF (1.5 mL) and THF (1.5 mL) was added NaH (30 mg, 60% pure, 0.75 mmol) at 0° C. The mixture was stirred for 30 minutes. Into the reaction mixture, compound from Example 7 (400 mg, 0.50 mmol) was added. The mixture was warmed to room temperature and stirred overnight. Additional imidazole (23 mg, (0.34 mmol) and NaH (10 mg, 0.25 mmol) were added. The mixture was stirred at room temperature for 10 more hours. The mixture was taken up in EtOAc, washed with water and then with brine and dried (Na$_2$SO$_4$), filtered and concentrated. The resulting crude residue was purified on silica gel (2M NH$_3$ in MeOH:CH$_2$Cl$_2$, 5:195) to give a 2:3 mixture of the desired compounds (200 mg, 58%).

MS (ESI) m/z 693 (M+H)$^+$.

Step 7b. A solution of a mixture of compounds from step 7a (42 mg) in MeOH (2 mL) was heated to 55° C. for 4 hours. The mixture was cooled to room temperature and concentrated under reduced pressure. The crude residue was purified on HPLC to give a mixture of the title compounds.

MS (ESI) m/z 651 (M+H)$^+$.

Example 8

Compounds of formulaes III and IV, wherein A and B taken together with the carbon atom to which they are attached are C=CH—CH=CH-phenyl, M is hydrogen, X and Y taken together with the carbon atom to which they are attached are C=N—Ac, L is ethyl, W is N(CH$_3$)$_2$, and R$_p$ is Ac.

A solution of a mixture of compounds from Example 7 (200 mg, 0.29 mmol), β-bromostyrene (106 mg, 0.58 mmol) and K$_2$CO$_3$ (160 mg, 1.16 mmol) in DMF (1 mL) was degassed by vacuum/N$_2$-fill method at −78° C. Into the mixture POPd (29 mg, 0.058 mmol) was added. The mixture was once again degassed and heated to 100° C. overnight. Additional β-bromostyrene (60 mg, 0.33 mmol) was added. The mixture was stirred at 100° C. for 8 hours. Another portion of β-bromostyrene (60 mg, 0.33 mmol) and additional POPd (10 mg, 0.02 mmol) were added. The mixture was stirred at 100° C. for 1 more day, cooled to room temperature, diluted with EtOAc, washed with an aqueous solution of saturated NaHCO$_3$, with brine and dried (Na$_2$SO$_4$), filtered and concentrated. The crude residue was purified on silica gel (acetone:hexanes, 60:40) to give the title compounds as an isomeric mixture.
MS (ESI) m/z 795 (M+H)$^+$.

Example 9

Compounds of formula III and IV, wherein A and B taken together with the carbon atom to which they are attached are C=CH—CH=CH-phenyl, M is hydrogen, X and Y taken together with the carbon atom to which they are attached are C=N—Ac, W is N(CH$_3$)$_2$, and R$_p$ is hydrogen.

A solution of a mixture of four isomers from Example 8 (190 mg) in MeOH (3 mL), was stirred at room temperature overnight. MeOH was removed under reduced pressure. The crude residue was purified by reverse-phase HPLC to give four different isomers in the amount of 13 mg, 8 mg, 12 mg, 20 mg.
MS (ESI) m/z 753 (M+H)$^+$.

Example 10

Compounds of formula III, wherein A is OH, B is CH$_2$OH, M is hydrogen, X and Y taken together with the carbon atom to which they are attached are C=N—Ac, L is ethyl, W is N(CH$_3$)$_2$ and R$_p$=Ac.

Into a solution of a mixture of compounds from Example 8 (40 mg) in tert-BuOH (0.2 mL) were added NMO (12.6 mg, 0.093 mmol) and OsO$_4$ (1 drop of 4% in H$_2$O). The mixture was stirred at room temperature for 45 minutes, taken up in EtOAc, washed with an aqueous solution of saturated NaHCO$_3$, then with brine and dried (Na$_2$SO$_4$), filtered and concentrated under reduced pressure. The crude residue was purified on silica gel (2M NH$_3$ in MeOH:CH$_2$Cl$_2$, 5:195) to give a 1:1 isomeric mixture of the title compound (17 mg).
MS (ESI) m/z 727 (M+H)$^+$.

Example 11

Compounds of formula III, wherein A is OH, B is CH$_2$OH, is hydrogen, X and Y taken together with the carbon atom to which they are attached are C=N—Ac, L is ethyl, W is N(CH$_3$)$_2$ and M and R$_p$ are hydrogen.

Compound from Example 10 was dissolved in MeOH and stirred at room temperature to give the title compound.

Example 12

Compounds of formula II, wherein A, V, and R$_{21}$ are OH, B is CH$_2$OH, M and U are hydrogen, X and Y taken together with the carbon atom to which they are attached are C=N—Ac, L is ethyl, W is N(CH$_3$)$_2$, R$_{20}$ is methyl, and R$_p$=Ac.

Obtained from the procedure of Example 10 as a 1:1 isomeric mixture (13 mg). MS (ESI) m/z 761 (M+H)$^+$.

Example 13

Compound of formula I, wherein A and B taken together with the carbon atom to which they are attached are C=CH$_2$, M is —C(O)N(CH$_2$CH=CH$_2$)(CONHCH$_2$CH=CH$_2$), X and Y taken together with the carbon atom to which they are attached are C=N—Ac, U and V taken together with the carbon atom to which they are attached are C=O, Z is F, L is ethyl, W is N(CH$_3$)$_2$, and R$_p$ is Ac.

To a solution of compound of formula (1-1, wherein A and B taken together with the carbon atom to which they are attached are C=CH$_2$, X and Y taken together with the carbon atom to which they are attached are C=N—Ac, U and V taken together with the carbon atom to which they are attached are C=O, Z=F, M is hydrogen, L is ethyl, W is N(CH$_3$)$_2$, and R$_p$ is Ac) (prepared according to U.S. application Ser. Nos. 10/429,485 and 10/436,60) (200 mg, 0.27 mmol) in THF (2.5 mL) was added allyl isocyanate (126 μL, 1.43 mmol) and CuI (catalytic amount) at room temperature. The mixture was stirred for about 2 hrs, then was diluted with CH$_2$Cl$_2$ and washed with saturated NaHCO$_3$ solution. The organic solution was dried (Na$_2$SO$_4$), filtered and concentrated under reduced pressure. The residue was purified by chromatography (silica, hexane:acetone 4:1 and 3:2) to give ~200 mg of the title compound.
MS (ESI) m/z=893 (M+H)$^+$.

Example 14

Compound of formula I, wherein A and B taken together with the carbon atom to which they are attached are C=CH$_2$, M is —C(O)N(CH$_2$CH=CH$_2$)(CONHCH$_2$CH=CH$_2$), X and Y taken together with the carbon atom to which they are attached are C=O, U and V taken together with the carbon atom to which they are attached are C=O, Z is F, L is ethyl, W is N(CH$_3$)$_2$, and R$_p$ is hydrogen.

A solution of the compound from Example 13 in THF (2 mL) and 3N HCl (2 mL) was heated at 80° C. for about 3 hours, evaporated to give the title compound.
MS (ESI) m/z=810 (M+H)$^+$.

Example 15

Compound of formula II, wherein A and B taken together with the carbon atom to which they are attached are C=CH$_2$, X and Y taken together with the carbon atom to which they are attached are C=NAc, U and V taken together with the carbon atom to which they are attached are C=O, M=R$_{20}$=H, R$_{21}$=CH$_2$OH, L is ethyl, W is N(CH$_3$)$_2$, and R$_p$=Ac.

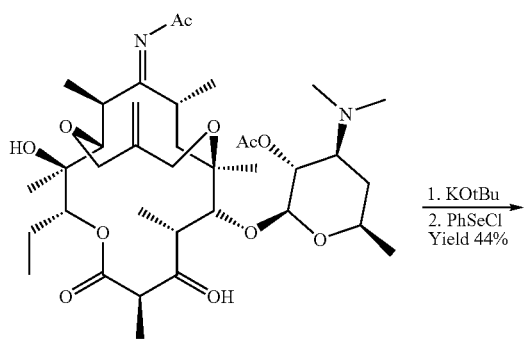

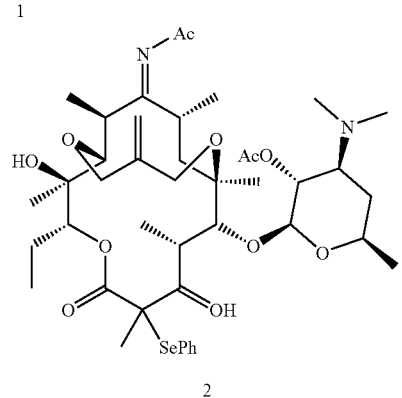

Step 15a. To a mixture of compound of formula (1-1, wherein A and B taken together with the carbon atom to which they are attached are C=CH$_2$, X and Y taken together with the carbon atom to which they are attached are C=N—Ac, U and V taken together with the carbon atom to which they are attached are C=O, M and Z are hydrogen, L is ethyl, W is N(CH$_3$)$_2$, and R$_p$ is Ac) (prepared according to U.S. application Ser. Nos. 10/429,485 and 10/436,60) (300 mg) in 3 ml of DMF, KO'Bu (75 mg) was added at 0° C. The reaction mixture was stirred at 0° C. for 50 min. phenylselenenyl chloride (135 mg) was then added. The cooling bath was removed and the reaction mixture was stirred at RT for 1 hour. The reaction mixture was then diluted with methylene chloride and washed with 1M NaHCO$_3$, water and brine. The organic layer was dried over Na$_2$SO$_4$, concentrated under vacuo and the residue was purified by flash column chromatography to give 163 mg of the desired product.

[M+H]: 865

Step 15b. The crude mixture from step 15a was dissolved in 20 ml of THF/H$_2$O (1:1). To this mixture was added Oxone (2.0 g). The resulted cloudy mixture was stirred at RT for 30 min. The reaction was then quenched with sodium bisulfite and extracted with methylene chloride, washed with 1M NaHCO$_3$, water and brine, dried, filtered and concentrated under vacuo. The residue was purified by flash column chromatography to give the title compound (273 mg).

[M+H]: 725

Example 16

Compound of formula II, wherein A and B taken together with the carbon atom to which they are attached are C=CH$_2$, X and Y taken together with the carbon atom to which they are attached are C=NAc, U and V taken together with the carbon atom to which they are attached are C=O, M=R$_{20}$=H, R$_{21}$=CH$_2$OCH$_3$, L is ethyl, W is N(CH$_3$)$_2$, and R$_p$ is hydrogen.

A solution of compound from Example 15 (20 mg) in methanol was heated to 55° C. for 2 hours. The excess methanol was evaporated off under vacuo to give the desired title compound.

[M+H]: 697.

Example 17

Compound of formula II, wherein A and B taken together with the carbon atom to which they are attached are C=CH$_2$, X and Y taken together with the carbon atom to which they are attached are C=NAc, U and V taken together with the carbon atom to which they are attached are C=O, M=R$_{20}$=H, R$_{21}$=CH$_2$—NH—O—CH$_2$-[5-(2-(pyrazol-1-yl)pyridine)], L is ethyl, W is N(CH$_3$)$_2$, and R$_p$ is hydrogen.

To a solution of compound from Example 15 (50 mg) in THF was added O-(6-pyrazol-1-yl-pyridin-3-ylmethyl)-hydroxylamine hydrochloride (prepared according to patent WO 03/097659) and the resulting mixture was stirred at room temperature for 2 days. The excess solvent was removed under vacuo and the residue was redissolved in methanol and was allowed to further stirred at room temperature overnight. The excess methanol was evaporated off and the residue was purified by HPLC to give the desired title compound.

[M+H]: 855.

Example 18

Compound of formula II, wherein A and B taken together with the carbon atom to which they are attached are C=CH$_2$, X and Y taken together with the carbon atom to which they are attached are C=NAc, U and V taken together with the carbon atom to which they are attached are C=O, M=R$_{20}$=R$_{21}$=H, L is ethyl, W is N(CH$_3$)$_2$, and R$_p$ is hydrogen.

A solution of compound from Example 15 (250 mg) in 10 ml of THF was added dropwise into a 1.3 L buffer of 0.2N NaOH in THF/H$_2$O (1:1) over 30 min. After 5 hours, THF was removed in vacuo. The aqueous solution was extracted with methylene chloride and washed with water and brine. The organic layer was dried over Na$_2$SO$_4$, filtered and concentrated under vacuo. The residue was purified by flash column chromatography to give the title compound (100 mg).

[M+H]: 653.

Example 19

Compound of formula II, wherein A and B taken together with the carbon atom to which they are attached are C=N—O—CH$_2$-[5-(2-(pyrazol-1-yl)pyridine)], X and Y taken together with the carbon atom to which they are attached are C=NAc, U and V taken together with the carbon atom to which they are attached are C=O, M=R$_{20}$=H, R$_{21}$=CH$_2$OH, L is ethyl, W is N(CH$_3$)$_2$, and R$_p$=Ac.

Step 19a. A solution of compound of formula (1-1, wherein A and B taken together with the carbon atom to which they are attached are C=N—O—CH$_2$-pyridyl-pyrazolyl, X and Y taken together with the carbon atom to which they are attached are C=N—Ac, U and V taken together with the carbon atom to which they are attached are C=O, M and Z are hydrogen, L is ethyl, W is N(CH$_3$)$_2$, and R$_p$ is Ac) (prepared according to U.S. application Ser. Nos. 10/429,485 and 10/436,60) (30 g, 34.0 mmol) in anhydrous DMF (100 ml) was cooled with ice-water bath to 0° C. To this solution was added solid 60 wt % NaH in mineral oil (2.2 equiv.) in portions. After stirring at 0° C. for 5 min, the ice bath was removed and the resulting suspension was allowed to slowly warm to room temperature over 60 min at which point a nice pale yellow slurry was formed and also no more gas evolution observed. The slurry was cooled back to 0° C. and then was added PhSeCl (1.1 equiv.). The reaction mixture was allowed to stir at 0° C. for 3 hours. After warming up to about 5-10° C., the reaction mixture was diluted with EtOAc (1.6 L). The mixture was washed with 50% aqueous NH$_4$Cl solution (450 ml), then with water (450 ml), dried over MgSO$_4$, and the organic solution was evaporated in vacuo to afford the crude product.

The residue was purified by flash column chromatography (acetone/hexanes, 1:1) to afford 70% of the desired selenylated compound.

[M+H]: 1039.

Step 19b. To a solution of oxone (10.65 g, 1.2 equiv.) in water (90 ml) at room temperature was slowly added a solution of the selenylated compound from step 19a (15.0 g, 1 equiv.) in THF (90 ml) over 10 min. The addition was slightly exothermic. The resulting pale yellow suspension was stirred at room temperature for an additional 20 min. The reaction was then quenched with a solution of sodium bisulfite (2.7 g, 1.2 equiv.) in water (10-15 ml) at <20° C. (with ice bath) to destroy the excess oxidant. The mixture was further stirred at 20-25° C. for 5 min. before saturated aqueous NaHCO$_3$ solution (120-150 ml) was added to neutralize the mixture to pH 8.5 to 9. The mixture was extracted with EtOAc twice (450 ml+150 ml). The combined organic phase was dried (MgSO$_4$) and subsequently evaporated in vacuo and the residue was purified by flash column chromatography eluting with 100% acetone to afford the title compound (8.2 g).

[M+H]: 899.

Example 20

Compound of formula II, wherein A and B taken together with the carbon atom to which they are attached are C=N—O—CH$_2$-[5-(2-(pyrazol-1-yl)pyridine)], X and Y taken together with the carbon atom to which they are attached are C=NAc, U and V taken together with the carbon atom to which they are attached are C=O, M=R$_{20}$=R$_{21}$=H, L is ethyl, W is N(CH$_3$)$_2$, and R$_p$=Ac.

To a 3M aqueous KOH solution (5.04 L) was added dropwise a solution of the compound from Example 19 (12.6 g) in CH$_2$Cl$_2$ (2.52 L) at 20-25° C. over 3.5 hrs. The resulting two-phase reaction mixture was agitated vigorously at 20-25° C. for 4 hrs. The reaction mixture was neutralized to a pH of 9.5-10.5 at 20-25° C. by slow addition of 36% HCl. The two-phase mixture was separated. The aqueous layer was extracted with CH$_2$Cl$_2$ (1.0 L). The combined organic solution was washed with water (0.75 L) then dried (MgSO$_4$) and subsequently evaporated in vacuo to dryness to afford the crude title compound which was purified by flash column chromatography (acetone/hexanes, 3:1) and then it was further purified by reverse-phase HPLC (20 mM aq. NH$_4$HCO$_3$-MeCN) to yield the title compound.

[M+H]: 869.
$^{13}$C NMR(CDCl$_3$, ppm) δ: 201.8, 183.7, 177.1, 162.9, 169.2, 153.4, 150.4, 147.6, 141.7, 138.7, 130.3, 126.8, 111.7, 107.4, 100.6, 79.4, 78.3, 76.1, 74.7, 73.8, 72.7, 71.2, 68.9, 63.1, 62.7, 62.2, 49.3, 45.0, 40.4, 40.0, 38.0, 36.7, 30.3, 24.8, 23.3, 21.2, 20.8, 19.8, 19.0, 17.2, 14.5, 13.4, 12.5.

Example 21

Compound of formula II, wherein A and B taken together with the carbon atom to which they are attached are C=N—O—CH$_2$-[5-(2-(pyrazol-1-yl)pyridine)], X and Y taken together with the carbon atom to which they are attached are C=NAc, U and V taken together with the carbon atom to which they are attached are C=O, M=R$_{20}$=R$_{21}$=R$_p$=H, L is ethyl, and W is N(CH$_3$)$_2$.

The title compound was prepared with the title compound of Example 20 via similar conditions described in Example 16.

[M+H]: 827.

Example 22

Compound of formula II, wherein A and B taken together with the carbon atom to which they are attached are C=N—O—CH$_2$-[5-(2-(pyrazol-1-yl)pyridine)], X and Y taken together with the carbon atom to which they are attached are C=NAc, U and V taken together with the carbon atom to which they are attached are C=O, M=R$_{20}$=H, R$_{21}$=CH$_2$CH=CH$_2$, L is ethyl, W is N(CH$_3$)$_2$, and R$_p$=Ac.

To a solution of compound from Example 20 in anhydrous THF at 0° C. was slowly added dropwise 1M KO$^t$BU (1.2 eq.) solution in THF. The mixture was vigorously stirred at 0° C. for 30 min before a 0.7 M solution of allyl bromide in THF was slowly added (1.0 equiv.). The resulting mixture was stirred at 0° C. for 60 min. After warming up to about 15° C., the mixture was diluted with EtOAc, washed with 5% aq. NH$_4$Cl solution, then with water. The organic solution was dried (MgSO$_4$) and evaporated to dryness and the residue was purified by column chromatography to give the desired product.

[M+H]: 909.

Example 23

Compound of formula II, wherein A and B taken together with the carbon atom to which they are attached are C=N—O—CH$_2$-[5-(2-(pyrazol-1-yl)pyridine)], X and Y taken together with the carbon atom to which they are attached are C=NAc, U and V taken together with the carbon atom to which they are attached are C=O, M=R$_{20}$=H, R$_{21}$=CH$_2$CH=CH$_2$, L is ethyl, W is N(CH$_3$)$_2$, and R$_p$ is hydrogen.

The title compound was prepared with the title compound of Example 22 via similar conditions described in Example 16.

[M+H]: 867.

Although the invention has been described with respect to various preferred embodiments, it is not intended to be limited thereto, but rather those skilled in the art will recognize that variations and modifications may be made therein which are within the spirit of the invention and the scope of the appended claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

What is claimed is:
1. A compound represented by formulaes:

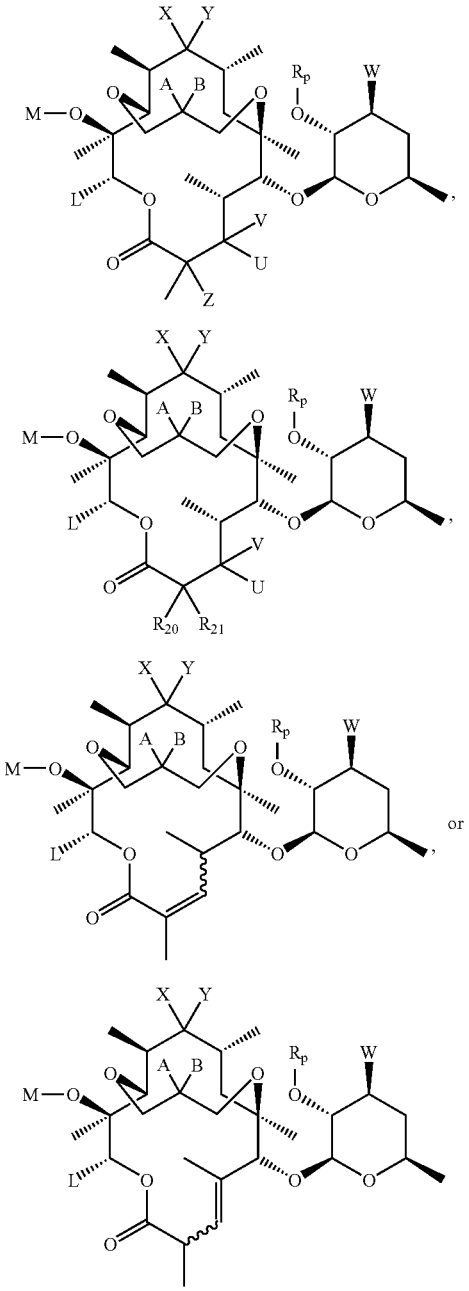

or their racemates, enantiomers, regioisomers, salts, esters or prodrugs thereof, wherein A and B are independently selected from the group consisting of: hydrogen, deuterium, halogen, $R_1$, $OR_1$, $S(O)_n R_1$, $-NR_1C(O)R_1$, $-NR_1C(O)NR_3R_4$, $-NHS(O)_nR_1$, $-CONR_3R_4$, and $NR_3R_4$;

$R_1$ and $R_2$ are independently selected from the group consisting of: hydrogen, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

Each of $R_3$ and $R_4$ is independently selected from the group consisting of: hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, a substituted, or unsubstituted heterocyclic group; or can be taken together with the nitrogen atom to which they are attached to form a substituted or unsubstituted heterocyclic or heteroaromatic ring;

Each of $R_{20}$ and $R_{21}$ is independently selected from the group consisting of: hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, a substituted, or unsubstituted heterocyclic group, provided that $R_{20}$ and $R_{21}$ cannot be methyl and hydrogen, methyl and methyl, or methyl and halogen;

or $R_{20}$ and $R_{21}$ taken together with the carbon atom to which they are attached form a substituted or unsubstituted alicylic or substituted or unsubstituted heterocyclic ring;

or A and B, taken together with the carbon atom to which they are attached, form a substituted or unsubstituted alicyclic, aromatic, heterocyclic or heteroaromatic ring;

or A and B, taken together with the carbon atom to which they are attached, are selected from the group consisting of: CO, $C=CHR_1$, $C=NR_1$, $C=NOR_1$, $C=NO(CH_2)_mR_1$, $C=NNHR_1$, $C=NNHCOR_1$, $C=NNHCONR_1R_2$, $C=NNHS(O)_nR_1$, and $C=N-N=CHR_1$;

M is selected from the group consist of: hydrogen, $R_1$, $C(O)R_1$, $S(O)_nR_1$, and $C(O)NR_3R_4$; provided that M is not hydrogen for compounds of formula I;

L is selected from the group consisting of: hydrogen, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, and a substituted or unsubstituted heterocyclic group;

X and Y are independently selected from the group consisting of: hydrogen, deuterium, halogen, $R_1$, $OR_1$, $S(O)_n R_1$, $-NR_1C(O)R_1$, $-NR_1C(O)NR_3R_4$, $-NR_1S(O)_nR_1$, $-C(O)NR_3R_4$, and $-NR_3R_4$;

or X and Y, taken together with the carbon atom to which they are attached, are selected from the group consisting of: CO, $C=CHR_1$, $C=NR_1$, $C=NC(O)R_1$, $C=NOR_1$, $C=NO(CH_2)_mR_1$, $C=NNHR_1$, $C=NNHCOR_1$, $C=NNHCONR_1R_2$, $C=NNHS(O)_nR_1$, $C=N-N=CHR_1$, $C=N-NO_2$, and $C=N-ONO$;

one of U or V is hydrogen and the other is independently selected from the group

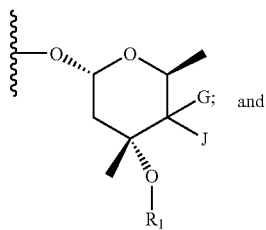

consisting of: $R_1$, $OR_1$, $OC(O)R_1$, $OC(O)NR_3R_4$, $S(O)_nR_1$, or U and V, taken together with the carbon atom to which they are attached, are C=O;

one of J or G is hydrogen and the other is selected from: $R_1$, $OR_1$, or $NR_3R_4$; or, J and G, taken together with the carbon atom to which they are attached, are selected from: C=O, C=$NR_1$, C=$NOR_1$, C=$NO(CH_2)_mR_1$, C=$NNHR_1$, C=$NNHCOR_1$, C=$NNHCONR_1R_2$, C=$NNHS(O)_nR_1$, or C=N—N=$CHR_1$;

W is $NR_3R_4$;

Z is hydrogen, alkyl or halogen;

$R_p$ is hydrogen, hydroxy protecting group or hydroxy prodrug group;

m is an integer; and n is 0, 1, or 2.

2. A compound of claim 1, wherein A and B taken together with the carbon atom to which they are attached are C=N—O—$CH_2$—$R_1$.

3. A compound of claim 2, wherein $R_1$ is a substituted pyridyl.

4. A compound of claim 2, wherein $R_1$ is a pyridyl substituted with pyrazole.

5. A compound of claim 2, wherein $R_1$ is —C≡C-(pyridyl) or —C≡C— (substituted pyridyl).

6. A compound of claim 2, wherein $R_1$ is —C≡C-(2-aminopyridyl).

7. A compound of claim 2, wherein $R_1$ is a pyridyl substituted with a substituted pyridyl.

8. A compound of claim 2, wherein $R_1$ is a substituted thiophenyl.

9. A compound of claim 2, wherein $R_1$ is a thiophenyl substituted with a substituted pyridyl.

10. A compound of claim 1, wherein A and B taken together with the carbon atom to which they are attached are C=CH—$R_1$.

11. A compound of claim 1, wherein A and B taken together with the carbon atom to which they are attached are C=$CH_2$.

12. A compound of claim 1, wherein X and Y taken together with the carbon atom to which they are attached are C=N—$R_1$.

13. A compound of claim 1, wherein X and Y taken together with the carbon atom to which they are attached are C=N—Ac.

14. A compound of claim 1, wherein A and B taken together with the carbon to which they are attached are C=O.

15. A compound of claim 1, wherein A and B taken together with the carbon to which they are attached are C=O and X and Y taken together with the carbon atom to which they are attached are C=N—$R_1$.

16. A compound of claim 1, wherein A and B taken together with the carbon to which they are attached are C=O and X and Y taken together with the carbon atom to which they are attached are C=N—Ac.

17. A compound claim 1, wherein A and B taken together with the carbon to which they are attached are C=O, X and Y taken together with the carbon atom to which they are attached are C=N—Ac, and W is $N(CH_3)_2$.

18. A compound of claim 1, wherein A and B taken together with the carbon atom to which they are attached are C=N—O—$R_1$, X and Y taken together with the carbon atom to which they are attached are C=N—$R_1$, L is ethyl, and W is $N(CH_3)_2$.

19. A compound of claim 1, wherein A and B taken together with the carbon atom to which they are attached are C=N—O—$CH_2$—$R_1$, X and Y taken together with the carbon atom to which they are attached are C=N=$R_1$, L is ethyl, and W is $N(CH_3)_2$.

20. A compound of claim 1 having the formula A:

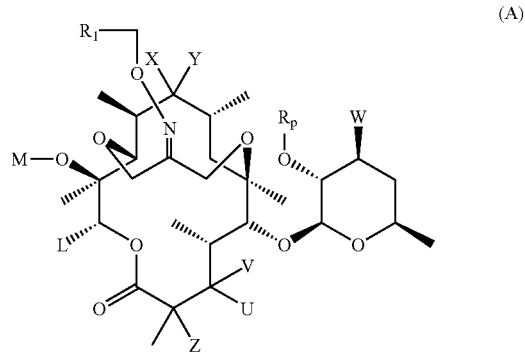

wherein X, Y, M, L, U, V, Z, W, $R_p$ and $R_1$ are as previously defined in claim 1.

21. A compound according to claim 1 selected from:
(1) compound of formula I, wherein A and B taken together with the carbon atom to which they are attached are C=N—O—$CH_2$-[5-(2-pyrazol-1-yl)pyridine)], M is —C(O)$NH_2$, X and Y taken together with the carbon atom to which they are attached are C=N—Ac, U and V taken together with the carbon atom to which they are attached are C=O, Z is hydrogen, L is ethyl, W is $N(CH_3)_2$, and $R_p$ is Ac;
(2) compound of formula I, wherein A and B taken together with the carbon atom to which they are attached are C=$CH_2$, M is —C(O)NH$CH_2$CH=$CH_2$, X and Y taken together with the carbon atom to which they are attached are C=N—Ac, U and V taken together with the carbon atom to which they are attached are C=O, Z is hydrogen, L is ethyl, W is $N(CH_3)_2$, and $R_p$ is hydrogen;
(3) compound of formula I, wherein A and B taken together with the carbon atom to which they are attached are C=N—O—$CH_2$-[5-(2-(pyrazol-1-yl)pyridine)], M is —$CH_2$CH=$CH_2$, X and Y taken together with the carbon atom to which they are attached are C=N—Ac, U is hydrogen, V is OH, Z is hydrogen, L is ethyl, W is $N(CH_3)_2$, and $R_p$ is Ac;
(4) compound of formula I, wherein A and B taken together with the carbon atom to which they are attached are C=N—O—$CH_2$-[5-(2-(pyrazol-1-yl)pyridine)], M is —$CH_2$CH=$CH_2$, X and Y taken together with the carbon atom to which they are attached are C=N—Ac, U is hydrogen, V is OH, Z is hydrogen, L is ethyl, W is $N(CH_3)_2$, and $R_p$ is Ac;
(5) compound of formula I, wherein A and B taken together with the carbon atom to which they are attached are C=N—O—$CH_2$-[5-(2-(pyrazol-1-yl)pyridine)], M is —CH$_2$CH=CH$_2$, X and Y taken together with the carbon atom to which they are attached are C=N—Ac, U and V taken together with the carbon atom to which they are attached are C=O, Z is hydrogen, L is ethyl, W is N(CH$_3$)$_2$, and R$_p$ is Ac;

(6) compound of formula I, wherein A and B taken together with the carbon atom to which they are attached are C=N—O—CH$_2$-[5-(2-(pyrazol-1-yl)pyridine)], M is —CH$_2$CH=CH$_2$, X and Y taken together with the carbon atom to which they are attached are C=N—Ac, U and V taken together with the carbon atom to which they are attached are C=O, Z is hydrogen, L is ethyl, W is N(CH$_3$)$_2$, and R$_p$ is hydrogen;

(7) compounds of formulaes III and IV, wherein A and B taken together with the carbon atom to which they are attached are C=CH$_2$, M is hydrogen, X and Y taken together with the carbon atom to which they are attached are C=N—Ac, L is ethyl, W is N(CH$_3$)$_2$, and R$_p$ is hydrogen;

(8) compounds of formulaes III and IV, wherein A and B taken together with the carbon atom to which they are attached are C=CH-CH=CH— phenyl, M is hydrogen, X and Y taken together with the carbon atom to which they are attached are C=N—Ac, L is ethyl, W is N(CH$_3$)$_2$, and R$_p$ is Ac;

(9) compounds of formula III and IV, wherein A and B taken together with the carbon atom to which they are attached are C=CH—CH=CH-phenyl, M is hydrogen, X and Y taken together with the carbon atom to which they are attached are C=N—Ac, W is N(CH$_3$)$_2$, and R$_p$ is hydrogen;

(10) compounds of formula III, wherein A is OH, B is CH$_2$OH, M is hydrogen, X and Y taken together with the carbon atom to which they are attached are C=N—Ac, L is ethyl, W is N(CH$_3$)$_2$ and R$_p$=Ac;

(11) compounds of formula III, wherein A is OH, B is CH$_2$OH, is hydrogen, X and Y taken together with the carbon atom to which they are attached are C=N—Ac, L is ethyl, W is N(CH$_3$)$_2$ and M and R$_p$ are hydrogen;

(12) compounds of formula II, wherein A, V, and R$_{21}$ are OH, B is CH$_2$OH, M and U are hydrogen, X and Y taken together with the carbon atom to which they are attached are C=N—Ac, L is ethyl, W is N(CH$_3$)$_2$, R$_{20}$ is methyl, and R$_p$=Ac;

(13) compound of formula I, wherein A and B taken together with the carbon atom to which they are attached are C=CH$_2$, M is —C(O)N(CH$_2$CH=CH$_2$) (CONHCH$_2$CH=CH$_2$), X and Y taken together with the carbon atom to which they are attached are C=N—Ac, U and V taken together with the carbon atom to which they are attached are C=O, Z is F, L is ethyl, W is N(CH$_3$)$_2$, and R$_p$ is Ac;

(14) compound of formula I, wherein A and B taken together with the carbon atom to which they are attached are C=CH$_2$, M is —C(O)N(CH$_2$CH=CH$_2$) (CONHCH$_2$CH=CH$_2$), X and Y taken together with the carbon atom to which they are attached are C=O, U and V taken together with the carbon atom to which they are attached are C=O, Z is F, L is ethyl, W is N(CH$_3$)$_2$, and R$_p$ is hydrogen;

(15) compound of formula II, wherein A and B taken together with the carbon atom to which they are attached are C=CH$_2$, X and Y taken together with the carbon atom to which they are attached are C=NAc, U and V taken together with the carbon atom to which they are attached are C=O, M=R$_{20}$=H, R$_{21}$=CH$_2$OH, L is ethyl, W is N(CH$_3$)$_2$, and R$_p$=Ac;

(16) compound of formula II, wherein A and B taken together with the carbon atom to which they are attached are C=CH$_2$, X and Y taken together with the carbon atom to which they are attached are C=NAc, U and V taken together with the carbon atom to which they are attached are C=O, M=R$_{20}$=H, R$_{21}$=CH$_2$OCH$_3$, L is ethyl, W is N(CH$_3$)$_2$, and R$_p$ is hydrogen;

(17) compound of formula II, wherein A and B taken together with the carbon atom to which they are attached are C=CH$_2$, X and Y taken together with the carbon atom to which they are attached are C=NAc, U and V taken together with the carbon atom to which they are attached are C=O, M=R$_{20}$=H, R$_{21}$=CH$_2$—NH—O—CH$_2$-[5-(2-(pyrazol-1-yl)pyridine)], L is ethyl, W is N(CH$_3$)$_2$, and R$_p$ is hydrogen;

(18) compound of formula II, wherein A and B taken together with the carbon atom to which they are attached are C=CH$_2$, X and Y taken together with the carbon atom to which they are attached are C=NAc, U and V taken together with the carbon atom to which they are attached are C=O, M=R$_{20}$=R$_{21}$=H, L is ethyl, W is N(CH$_3$)$_2$, and R$_p$ is hydrogen;

(19) compound of formula II, wherein A and B taken together with the carbon atom to which they are attached are C=N—O—CH$_2$-[5-(2-pyrazol-1-yl)pyridine)], X and Y taken together with the carbon atom to which they are attached are C=NAc, U and V taken together with the carbon atom to which they are attached are C=O, M=R$_{20}$=H, R$_{21}$=CH$_2$OH, L is ethyl, W is N(CH$_3$)$_2$, and R$_p$=Ac;

(20) compound of formula II, wherein A and B taken together with the carbon atom to which they are attached are C=N—O—CH$_2$-[5-(2-(pyrazol-1-yl)pyridine)], X and Y taken together with the carbon atom to which they are attached are C=NAc, U and V taken together with the carbon atom to which they are attached are C=O, M=R$_{20}$=R$_{21}$=H, L is ethyl, W is N(CH$_3$)$_2$, and R$_p$=Ac;

(21) compound of formula II, wherein A and B taken together with the carbon atom to which they are attached are C=N—O—CH$_2$-[5-(2-(pyrazol-1-yl)pyridine)], X and Y taken together with the carbon atom to which they are attached are C=NAc, U and V taken together with the carbon atom to which they are attached are C=O, M=R$_{20}$=R$_{21}$=R$_p$=H, L is ethyl, and W is N(CH$_3$)$_2$;

(22) compound of formula II, wherein A and B taken together with the carbon atom to which they are attached are C=N—O—CH$_2$-[5-(2-(pyrazol-1-yl)pyridine)], X and Y taken together with the carbon atom to which they are attached are C=NAc, U and V taken together with the carbon atom to which they are attached are C=O, M=R$_{20}$=H, R$_{21}$=CH$_2$CH=CH$_2$, L is ethyl, W is N(CH$_3$)$_2$, and R$_p$=Ac;

(23) compound of formula II, wherein A and B taken together with the carbon atom to which they are attached are C=N—O—CH$_2$-[5-(2-(pyrazol-1-yl)pyridine)], X and Y taken together with the carbon atom to which they are attached are C=NAc, U and V taken together with the carbon atom to which they are attached are C=O, M=R$_{20}$=H, R$_{21}$=CH$_2$CH=CH$_2$, L is ethyl, W is N(CH$_3$)$_2$, and R$_p$ is hydrogen.

22. A pharmaceutical composition comprising a therapeutically effective amount of a compound of claim 1 or a pharmaceutically-acceptable salt, ester or prodrug thereof, in combination with a pharmaceutically acceptable carrier.

23. A method for treating a bacterial infection in a subject in need of such treatment, comprising administering to said subject a therapeutically-effective amount of a pharmaceutical composition according to claim 22.

24. A method of treating cystic fibrosis in a patient, comprising administering to said subject, a therapeutically effective amount of a pharmaceutical composition of claim 22.

25. A method of treating inflammation in a subject comprising administering to said subject, therapeutically effective amount of a pharmaceutical composition of claim 22.

* * * * *

UNITED STATES PATENT AND TRADEMARK OFFICE
CERTIFICATE OF CORRECTION

PATENT NO. : 7,414,030 B2  
APPLICATION NO. : 11/029640  
DATED : August 19, 2008  
INVENTOR(S) : Nha Huu Vo et al.

It is certified that error appears in the above-identified patent and that said Letters Patent is hereby corrected as shown below:

On the title page item [75] under the Inventors section:  
Ly Tam Phan, please delete "Quing, MA" and replace with --Quincy, MA--;  
Zhe Wang, please delete "Hockessin (DE)" and replace with --Hockessin DE (US)--.

Column 46  
Claim 1, Line 45, please delete "group consist of" and replace with --group consisting of--.

Column 47  
Claim 1, Lines 1-13: please delete " 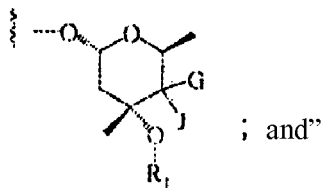 ; and"

Claim 1, Line 13: after "S(O)nR1," add -- and 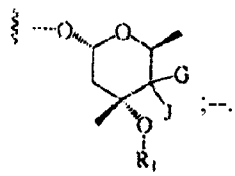 ;--.

Column 48  
Claim 17, Line 1, please insert --of-- after "compound;"  
Claim 19, Line 13, please delete "C=N=R1" and replace with --C=N-R1--.

Signed and Sealed this

Seventeenth Day of March, 2009

JOHN DOLL  
*Acting Director of the United States Patent and Trademark Office*